US008128952B2

(12) United States Patent
Metters et al.

(10) Patent No.: US 8,128,952 B2
(45) Date of Patent: Mar. 6, 2012

(54) LIGAND-MEDIATED CONTROLLED DRUG DELIVERY

(75) Inventors: Andrew T. Metters, Clemson, SC (US); Srinivas Chollangi, Norman, OK (US)

(73) Assignee: Clemson University Research Foundation, Clemson, SC (US)

( * ) Notice: Subject to any disclaimer, the term of this patent is extended or adjusted under 35 U.S.C. 154(b) by 1069 days.

(21) Appl. No.: 11/034,437

(22) Filed: Jan. 12, 2005

(65) Prior Publication Data
US 2006/0153919 A1    Jul. 13, 2006

(51) Int. Cl.
*A61F 2/00* (2006.01)
(52) U.S. Cl. ......... 424/423; 424/426; 424/486; 424/490
(58) Field of Classification Search .................. None
See application file for complete search history.

(56) References Cited

U.S. PATENT DOCUMENTS

| | | | |
|---|---|---|---|
| 4,526,938 A | 7/1985 | Churchill et al. | |
| 4,666,704 A | 5/1987 | Shalati et al. | |
| 5,434,146 A | 7/1995 | Babrie et al. | |
| 5,492,937 A | 2/1996 | Bogentoft et al. | |
| 5,693,341 A | 12/1997 | Schroeder et al. | |
| 5,702,717 A | 12/1997 | Cha et al. | |
| 5,830,986 A | 11/1998 | Merrill et al. | |
| 5,840,338 A | 11/1998 | Roos et al. | |
| 5,900,238 A | 5/1999 | Gombotz et al. | |
| 5,952,232 A | 9/1999 | Rothman | |
| 6,040,295 A | 3/2000 | Rolland et al. | |
| 6,083,534 A | 7/2000 | Wallach et al. | |
| 6,103,528 A | 8/2000 | An et al. | |
| 6,110,498 A | 8/2000 | Rudnic et al. | |
| 6,113,947 A | 9/2000 | Cleland et al. | |
| 6,123,861 A | 9/2000 | Santini, Jr. et al. | |
| 6,153,211 A * | 11/2000 | Hubbell et al. | 424/426 |
| 6,156,348 A | 12/2000 | Santos et al. | |
| 6,197,577 B1 | 3/2001 | Jeffrey et al. | |
| 6,284,276 B1 | 9/2001 | Rudnic et al. | |
| 6,287,599 B1 | 9/2001 | Burnside et al. | |
| 6,290,729 B1 | 9/2001 | Slepian et al. | |
| 6,333,194 B1 | 12/2001 | Levy et al. | |
| 6,395,299 B1 | 5/2002 | Babich et al. | |
| 6,423,345 B2 | 7/2002 | Bernstein et al. | |
| 6,451,346 B1 | 9/2002 | Shah et al. | |
| 6,482,413 B1 | 11/2002 | Chalasani et al. | |
| 6,511,650 B1 | 1/2003 | Eiselt et al. | |
| 6,514,518 B2 | 2/2003 | Monkhouse et al. | |
| 6,538,089 B1 | 3/2003 | Samra et al. | |
| 6,562,617 B1 | 5/2003 | Anderson et al. | |
| 6,613,082 B2 | 9/2003 | Yang | |
| 6,632,457 B1 | 10/2003 | Sawhney | |
| 6,652,873 B2 | 11/2003 | Deaver et al. | |
| 6,689,390 B2 | 2/2004 | Bernstein et al. | |
| 6,692,738 B2 | 2/2004 | MacLaughlin et al. | |
| 6,696,089 B2 | 2/2004 | Kabanov et al. | |
| 6,699,504 B2 | 3/2004 | Rowe et al. | |
| 6,723,344 B2 | 4/2004 | Sakiyama-Elbert et al. | |
| 6,730,322 B1 | 5/2004 | Bernstein et al. | |
| 6,743,446 B2 | 6/2004 | Schwendeman et al. | |
| 6,841,617 B2 | 1/2005 | Jeong et al. | |
| 2001/0020086 A1 | 9/2001 | Hubbell et al. | |
| 2002/0086829 A1 * | 7/2002 | Gefter | 514/12 |
| 2003/0082225 A1 | 5/2003 | Mason | |
| 2003/0119186 A1 | 6/2003 | Hubbell et al. | |
| 2003/0187232 A1 | 10/2003 | Hubbell et al. | |
| 2004/0033264 A1 | 2/2004 | Sawhney | |
| 2004/0072961 A1 | 4/2004 | Pathak et al. | |
| 2004/0086493 A1 | 5/2004 | Hubbell et al. | |

OTHER PUBLICATIONS

The term "predetermine"—Merriam-Webster Online Dictionary, at the web- http://www.m-w.com, p. 1.*
Wetering P. van de et al. Poly(ethylene glycol) hydrogels formed by conjugate addition with controllable swelling, degradation, and release of pharmaceutically active proteins, Journal of Controlled Release, 2005, 102: 619-627 (published online Dec. 9, 2004), entire document.*
Fassina G. et al. Protein A mimetic peptide ligand for affinity puriifcation of antibodies, Journal of Molecular Recognition, 1996, vol. 9, pp. 564-569, entire document.*
Wu D. et al. "Synthesis, characterization and drug release from three-arm poly(epsilon-caprolactone) maleic acid/poly(ethylene glycol) diacrylate hydrogels", J. Biomater. Sci. Polymer. Edn., 2003, vol. 14, No. 8, pp. 777-802, entire document.*
Boyd L.F. et al. Solution binding of an antigenic peptide to a major histocompatibility complex class I molecule and the role of beta2-microglubulin, proc. Natl. Acad. Sci., USA, Mar. 1992, vol. 89, pp. 2242-2246.*
Palombo G. et al. Affinity purification of immunoglobulin M using a novel synthetic ligand, Journal of Chromatography B, 1998, vol. 715, pp. 137-145.*
Abstract of Article entitled *Biodegradation biocompatibility of PLA and PLGA microspheres*, M. S. Shive and J. M. Anderson, Adv. Drug Deliv. Rev., vol. 28, No. 1, Oct. 13, 1997, pp. 5-24.
Article—*Biodegradation and In Vivo Biocompatibility of Rosin: a Natural Film-Forming Polymer*, Prashant M. Satturwar, Suniket V. Fulzele, and Avinash K. Dorle, AAPS PharmSciTech, vol. 4, Article 55, 2003, pp. 1-6.
Article—*Chemotherapy of Mycobacterium tuberculosis infections in mice with a combination of isoniazid and rifampicin entrapped in Poly (DL-lactide-co-glycolide) microparticles*, Manisha Dutt and G. K. Khuller, Journal of Antimicrobial Chemotherapy, vol. 47, 2001, pp. 829-835.

(Continued)

*Primary Examiner* — Sue Liu
*Assistant Examiner* — Satyendra Singh
(74) *Attorney, Agent, or Firm* — Dority & Manning, P.A.

(57) ABSTRACT

Disclosed are systems and methods that can be utilized to define and control the delivery rate of a biological agent from a carrier matrix such as a biocompatible hydrogel. The carrier matrices of the present invention can include ligands incorporated within the matrix at a predetermined concentration level ($C_{LT}$). In addition, the ligands within the matrix can display a particular, predetermined affinity for the biologically active agents to be delivered by the system. In particular, the affinity between the ligand and the biologically active agent can have a known predetermined dissociation constant ($K_D$). When utilizing the system, the agent can be incorporated within the matrix due to association of the agent with the ligand. In addition, the agent can be protected from side reactions due to the association of the agent with the ligand. Through particular selection of the parameters $C_{LT}$ and $K_D$, the rate of release of the biologically active agent from the matrix can be controlled. The disclosed methods and systems can be advantageously used in both in vivo clinical settings and ex vivo settings, such as tissue engineering applications.

42 Claims, 11 Drawing Sheets

OTHER PUBLICATIONS

Article—*Development of a multifunctional matrix drug delivery system surrounded by an impermeable cylinder*, I. Krögel and R. Bodmeier, Journal of Controlled Release, vol. 61, 1999, pp. 43-50.

Article—*Development of fibrin derivatives for controlled release of heparin-binding growth factors*, Shelly E. Sakiyama-Elbert and Jeffrey A. Hubbell, Journal of Controlled Release, vol. 64, 2000, pp. 389-402.

Article—*Enhancement & Controlled Release as Synergistic Tools*, Jones W. Bryan, Drug Delivery Technology, vol. 2, No. 6, 2002, 14 pages, www.drugdeliverytech.com.

Article—*Hyaluronan microspheres for sustained gene delivery and site-specific targeting*, Yang H. Yun, Douglas J. Goetz, Paige Yellen, and Weiliam Chen, Biomaterials, vol. 25, 2004, pp. 147-157.

Article—*In situ forming degradable networks and their application in tissue engineering and drug delivery*, Kristi S. Anseth, Andrew T. Metters, Stephanie J. Bryant, Penny J. Martens, Jennifer H. Elisseeff, and Christopher N. Bowman, Journal of Controlled Release, vol. 78, 2002, pp. 199-209.

Article—*Predicting Controlled-Release Behavior of Degradable PLAb-PEG-b-PLA Hydrogels*, Mariah N. Mason, Andrew T. Metters, Christopher N. Bowman, and Kristi S. Anseth, Macromolecules, vol. 34, 2001, pp. 4360-4635.

Article—*Release Behavior of High Molecular Weight Solutes from Poly(ethylene glycol)-Based Degradable Networks*, Sanxiu Lu and Kristi S. Anseth, Macromolecules, vol. 33, No. 7, 2000, pp. 2509-2515.

Article—*Superporous Hydrogels for Pharmaceutical & Other Applications*, Kinam Park, Drug Delivery Technology, vol. 2, No. 5, 2002, 11 pages, www.drugdeliverytech.com.

Article—*Sustained Release Drug Delivery Systems in Management of Tuberculosis*, G. K. Khuller and Rajesh Pandey, Indian J. Chest. Dis. Allied Sci., vol. 45, 2003, pp. 229-230.

Article—*Tailoring the Swelling Pressure of Degrading Dextran Hydroxyethyl Methacrylate Hydrogels*, Barbara G. Stubbe, Ferenc Horkay, Brian Amsden, Wim E. Hennink, Stefaan C. De Smedt, and Jo Demeester, Biomacromolecules, vol. 4, No. 3, 2003, pp. 691-695.

Abstract entitled: *Controlled Release of Ligand Immobilized Drug Molecules from Polymeric Scaffolds: A Predictive Model* by Chollangi, S., and Metters, A. Southeast Workshop on Tissue Engineering and Biomaterials, Clemson University, Jan. 29, 2004.

Abstract entitled: *Controlled Release of Ligand Immobilized Drug Molecules from Polymeric Scaffolds: A Predictive Model* by Chollangi, S., and Metters, A., Mar. 31, 2004.

Poster entitled: *Controlled Release of Ligand Immobilized Drug Molecules from Polymeric Scaffolds: A Predictive Model* by Chollangi, S., and Metters, A. at the American Chemical Society Spring Meeting, Anaheim, California, Mar. 31, 2004.

Article—*Solute Diffusion in Swollen Membranes. IX. Scaling Laws for Solute Diffusion in Gels*, Steven R. Lustig and Nikolaos A. Peppas, Journal of Applied Polymer Science, vol. 36, 1988, pp. 735-747.

Article—*Interaction of human immunoglobulin G with L-histidine immobilized onto poly(ethylene vinyl alcohol) hollow-fiber membranes*, Karsten Haupt, Sonia M. A. Bueno, and M. A. Vijayalakshmi, Journal of Chromatography B, vol. 674, 1995, pp. 13-21.

Article—*Correlation between mesh size and equilibrium degree of swelling of polymeric networks*, T. Canal and N. A. Peppas, J. Biomed. Mater. Res., vol. 23, No. 10, 1989, pp. 1183-1193.

Article—*Graft copolymer compositions that exhibit temperature-induced transitions over a wide range of pH*, Chen, G.H. and A.S. Hoffman, Nature vol. 373, 1995, pp. 49-52.

Article—*Integrin Interactions with Immobilized Peptides in Polyethylene Glycol Diacrylate Hydrogels*, Gonzalez et al., Tissue Engineering, vol. 10, No. 11/12, 2004, pp. 1775-1896.

International Search Report; PCT/US06/00794; Jun. 17, 2008.

* cited by examiner

LIGAND-MEDIATED CONTROLLED DRUG DELIVERY

BACKGROUND OF THE INVENTION

In an attempt to develop sustained release delivery systems, polymeric matrices have been widely investigated as possible carriers of a variety of biologically active agents. Problems in forming viable polymeric systems for delivery of many types of agents have been difficult to overcome, however. For example, polymeric carrier matrices have often been loaded with biologically active agents by either development of a crosslinked matrix in the presence of the agent or by swelling a pre-formed, crosslinked polymer in a solution of the agent. Problems with such systems include reaction and subsequent inactivation of the unprotected agent during and following gel loading as well as problems due to solubility limitations, as many biologically active agents are only sparingly soluble in aqueous environments and thus must be loaded into a pre-existing hydrogel in a non-aqueous environment. Unfortunately, many of the biologically active agents of interest will be denatured or otherwise inactivated in such a non-aqueous environment.

Usefulness of existing matrix delivery systems in achieving slow and controlled release of loaded materials has also been limited. For instance, delivery rates of the loaded materials from existing systems have been estimated based primarily upon diffusion rates of the biologically active agents within the encapsulating matrix and/or degradation rate of the matrix itself. Due to the extreme sensitivities of solute diffusivities to various matrix and solute properties as well as system variations that can occur during matrix fabrication, poor control over delivery rates of agents from existing systems has been obtained. Problems with existing systems include initial 'bursts' of drugs released in large and uncontrollable quantities; non-constant or pulsatile delivery of materials from the carrier matrix; continuously decreasing release rates (first-order release profiles); unacceptably fast delivery of materials from the carrier matrix; and/or low release efficiency due to reaction of the materials with the matrix components.

Methods have been attempted to slow the release of the agents from the matrices. Development of matrix networks with smaller mesh sizes and therefore lower solute permeabilities has been examined in an attempt to slow the release rates of the agents encapsulated within the networks. The releasable solute itself has also been modified in attempts to slow its release. For example, chemical derivatization of the agents in the form of 'prodrugs' has been used to bind as well as to protect the agent within the matrix. Other methods have included development of a two-phase carrier matrix with the active agent sequestered within one of the phases as well as development of particular network characteristics in the carrier matrix. For example, utilization of heparin incorporation into a drug delivery matrix has been suggested in U.S. Patent Application Publication 2003/0187232 to Hubbell, et al., and U.S. Pat. No. 6,723,344 to Sakiyama-Elbert, et al., so as to non-covalently bind a drug to the heparin and slow the diffusion rate of the drug within the matrix. However, the disclosed processes often involve chemical derivatization of the drugs so as to develop the necessary heparin-binding capability in the materials. In addition, while such systems may slow drug delivery as compared to pure, diffusion-based drug delivery, they still do not provide any methods for controlling or predetermining a particular drug delivery rate. In effect, such systems provide at most an inherent drug delivery rate with little or no control options.

Other problems exist with existing systems, as well. For example, derivatization of a biologically active agent is undesirable due to the unpredictable effect of the chemical change on agent toxicity and overall pharmacokinetics of the derivatized agents. Development of two-phase networks or networks formed of polymers including very particular blocks or materials can get expensive and complicated, and these networks are often limited to utilization with quite small biologically active agents. Development of small mesh sizes in carrier matrices also presents formation difficulties. For example, compact networks display increased hydrophobicity, which can increase the immune response of an individual to the carrier.

What is needed in the art are methods and systems that can provide controlled, sustained release of a biologically active agent from a carrier matrix with a predetermined and controllable rate of release without necessity of modifying the chemical or physical nature of the deliverable agent.

SUMMARY OF THE INVENTION

In general, the present invention is directed to methods and systems that can be utilized for delivering a biologically active agent from a polymeric matrix with a predetermined rate of release. According to the presently disclosed methods, a ligand can be selected that has an affinity for the biologically active agent to be delivered by the system. In particular, the ligand can be selected according to a predetermined dissociation constant ($K_D$) describing this affinity and the ligand can be incorporated into the polymeric matrix at a predetermined concentration level. The rate of release of the biologically active agent from the polymeric matrix established upon incorporation of the agent into the matrix can then be controlled according to these particular parameters, i.e., $K_D$ and the concentration of the ligand. For instance, in one embodiment, $K_D$ can be less than about 1.0E+1 mM. In another embodiment $K_D$ can be less than about 1.0E-5 mM, for example, between about 1.0E-9 mM and about 1.0E-5 mM.

The polymeric matrix can generally be any suitable carrier matrix and selection can usually depend upon the final use of the system. For example, in one embodiment the matrix can be a hydrogel matrix. This hydrogel matrix can be in the form of a thin film or slab, injectable microspheres or nanospheres, or an arbitrarily shaped drug depot that can be formed, for example, in situ after being injected into a void or defect site. If desired, the matrix can be a degradable hydrogel matrix, such as may be used for in vivo drug delivery. In one embodiment, the rate of degradation of the hydrogel matrix can also be a determining factor in the release rate of the biologically active agent from the matrix.

In one embodiment, the polymeric matrix can be a tissue-engineering scaffold. For example, the polymeric matrix can also encapsulate living cells, and the biologically active agents carried in the matrix can be delivered from the matrix to the living cells at the interface of the matrix with the cells. According to one embodiment, the matrix can also include cell membrane receptor ligands having an affinity for the living cells encapsulated by the matrix so as to encourage the healthy development of the cells held in the matrix.

In one embodiment, the polymeric matrix of the invention can define a homogeneous gel with relatively large mesh or pore size, for example, many times greater than the size of the therapeutic agent (e.g., greater than 5 nm in one embodiment). In another embodiment, the polymeric matrix of the invention can define a heterogeneous network including pore sizes on the order of microns, for example between approximately 1 µm and about 100 µm. According to certain embodiments, the disclosed methods and systems may be particularly suitable for delivery of macromolecular biologically active agents with molecular weights ranging from 1 kDa to 200 kDa. For instance entire proteins can be carried and delivered from the systems in a controlled fashion, and in one particular embodiment, entire unmodified protein therapeutics can be carried and delivered according to the invention.

The ligands that can be bound within the polymeric matrix can be natural or synthetic ligands (or chimeras thereof). For example, in one embodiment, a synthetic ligand comprising a particular peptide sequence can be constructed according to a combinatorial synthesis method so as to display a particular dissociation constant with the agent to be delivered from the system. A particular ligand with a predetermined, pre-selected affinity for the releasable drug can be constructed in this manner and incorporated into systems for releasing the drug at a predetermined, controllable rate.

Through utilization of the disclosed methods and systems, the release profile of the biologically active agent can be defined and controlled. For example, in one embodiment, the release of the agent can be extended over a much longer timeframe than has been possible with previously known systems. In another embodiment, a zero order release profile can be designed through particular selection of the type and concentration of the ligand included in the matrix. In another embodiment, the rate of release of the agent from the matrix can describe a biphasic release profile.

In one embodiment of the invention, a ligand/agent complex can be formed and the biologically active agent can be incorporated into the carrier matrix in the complex form. According to this embodiment, not only can the release rate of the agent from the ligand be controlled as described, but the agent can also be protected from reaction with the matrix and/or the matrix components during the formation and/or delivery process. For instance, in one particular embodiment, the drug release efficiency of the agent from the system can be increased due to the formation of the complex and the associated protection of the agent from detrimental interaction with the matrix and/or matrix components.

In one embodiment, the methods and systems of the invention can be utilized to deliver two or more biologically active agents from a single matrix, and each agent can be delivered according to its own release rate, one or both of which can be independently controlled through selection of the type and concentration of the ligand used to hold each agent in the matrix.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, in which.

DEFINITIONS OF TERMS

Figure 1:
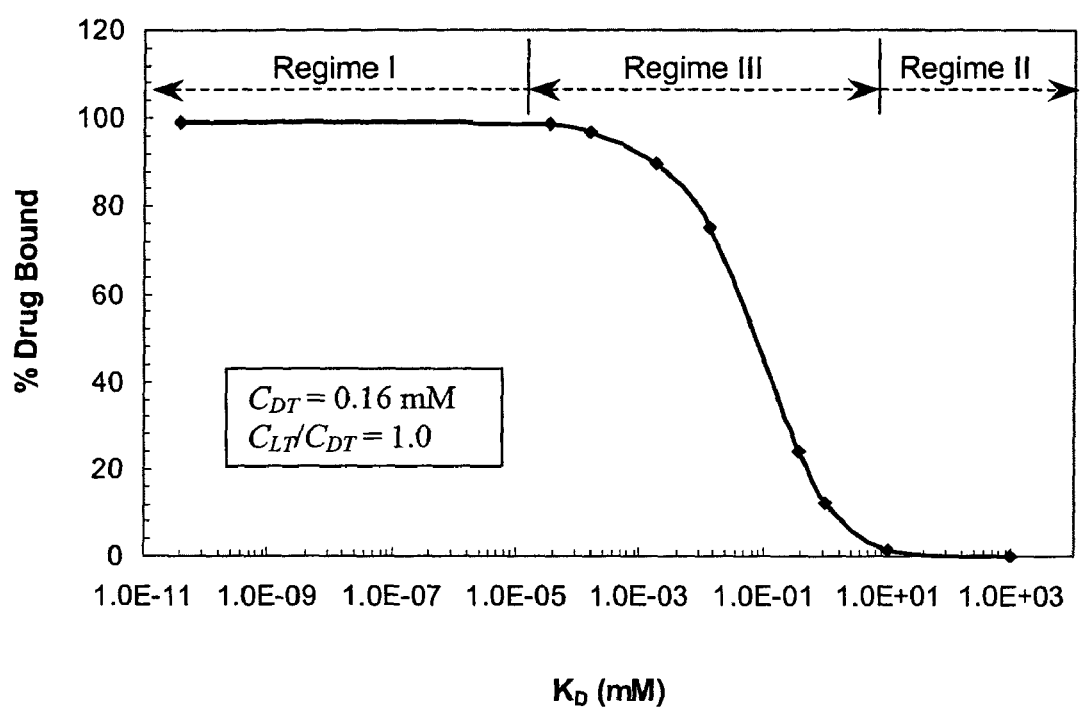
FIG. 1 shows the predicted effect of the strength of drug-ligand binding (quantified through its dissociation constant, $K_D$) on the percent drug binding to a non-degradable or substantially non-degradable matrix.

"Peptide" and "polypeptide" are herein defined to indicate a molecular chain of amino acids and does not refer to a specific length of the product. Thus, peptides, oligopeptides and proteins are included within the definition of polypeptide. This term is also intended to include polypeptides that have been subjected to post-expression modifications such as, for example, glycosylations, acetylations, phosphorylations and the like.

For purposes of this disclosure, the term "protein" is herein defined to include any molecular chain of amino acids that is capable of interacting structurally, enzymatically or otherwise with other proteins, polypeptides or any other organic or inorganic molecule.

The term "oligonucleotide" is herein defined to indicate a molecular chain of nucleic acids, and does not refer to a specific length of product nor to any specific backbone construction. In particular, the present invention is not limited to oligonucleotides constructed in the fashion of naturally occurring oligonucleotides, i.e., DNA and RNA constructions. For instance, in certain embodiments, oligonucleotides which include a variety of different backbone modifications can be utilized. In general, any oligonucleotide which can form the DNA-like hydrogen base pair recognition interaction is included in the term.

According to the present disclosure, the term "small molecule" in reference to a biologically active agent is herein defined as any agent with a molecular weight less than approximately 500 Da that can be used to obtain a beneficial therapeutic effect. The term encompasses small molecule drugs (i.e., low molecular weight therapeutic agents), imaging agents, and other low molecular weight chemical compounds used in medical technologies. In particular, the term is not intended to be limited to only therapeutic agents, but is intended to encompass any low molecular weight agent that can exhibit a beneficial biological activity.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used in another embodiment to yield a still further embodiment. Thus, it is intended that the present invention cover such modifications and variations as come within the scope of the appended claims and their equivalents.

The present invention is generally directed to methods that can be utilized to define and control the delivery rate of a biological agent from a carrier matrix and systems incorporating the control mechanisms. The ability to provide controlled, sustained delivery of biologically active agents to a biological system such as may be provided by the present invention is desirable to better regulate the pharmacodynamics and efficacy of therapeutic agents delivered in clinical settings as well as to encourage healthy tissue growth and formation in tissue engineering applications. For instance, sustained release delivery methods and systems such as those disclosed herein that can protect drugs from in vivo degradation and/or provide slow, well-controlled, and localized drug delivery to individual patients have numerous advantages over more traditional delivery methods. For example, such systems can increase the time between necessary treatments, maintain proper drug concentrations in the patient's blood or at the effect site between treatments, and increase the percentage of drug delivered in the appropriate therapeutic window. These advantages can in turn minimize the number of treatments, decrease patient discomfort and increase patient compliance with treatment protocols.

According to the present invention, drug delivery systems are provided that can include ligands incorporated within a matrix at a predetermined concentration level ($C_{LT}$). In addition, the ligands within the matrix can display a particular affinity for the biologically active agents to be delivered by the system. In particular, a ligand can be selected that describes a known, predetermined dissociation constant ($K_D$) with the biologically active agent at the equilibrium condition of the complex formed upon the association of the ligand with the agent. According to one embodiment, the agent can be incorporated within the matrix at a concentration, $C_{DT}$, through a non-covalent, reversible association of the agent with the ligand. The release rate of the biologically active agent from ligand, and, in certain embodiments, from the matrix itself, can be predetermined and controlled according to the values of the particular parameters $C_{LT}/C_{DT}$ and $K_D$. For instance, according to embodiments of the present invention, the release rate of a biologically active agent from a carrier matrix can be designed so as to approach a zero-order release profile.

In addition, as the ligand is selected based upon its particular affinity with the biologically active agent to be delivered by the system, the agent can be associated with the ligand in an unmodified state, with no potentially detrimental chemical derivatization of the agent required in order to provide an artificial affinity between the two components. Moreover, in certain embodiments, during the time that the biologically active agent is associated with the ligand, it can be held in an essentially unreactive state to the matrix materials. Thus, through the ligand selection, an unmodified agent can be protected from side reaction during formation of the system as well as during the delivery process. As such, the agent can maintain its known and desired bioactivity during and following the delivery process and improved drug release efficiency can be attained from the disclosed systems.

The methods and systems of the invention are suitable for both in vivo and in vitro applications. For instance, in one embodiment, the disclosed systems can be utilized in treatment or prevention of disease in an individual, providing sustained, controlled delivery of an agent to a patient and, optionally, targeting delivery of the agent to a particular cell type or tissue type. The disclosed systems and methods can be particularly effective for in vivo utilization with hydrophilic, macromolecular, and environmentally sensitive agents such as peptide and protein therapeutics as well as biologically active agents such as oligonucleotides and polysaccharides.

In another embodiment, the disclosed invention can be utilized in vitro, for instance in tissue engineering applications. For example, the systems and methods of the invention can be utilized to provide for the controlled release of nutrient and growth materials or specific biologically active molecules to a developing cellular system that can be held in or associated with the matrix. The release rate control provided by the invention can be beneficial even when utilizing a highly permeable or porous carrier matrix such as the highly swollen and hydrophilic hydrogel networks that are becoming particularly attractive in the field of tissue generation and tissue regeneration.

The polymeric carrier matrix of the disclosed systems can, in one embodiment, be a biocompatible matrix as is generally known in the art. For instance, in one embodiment, the carrier matrix can be a single-phase biocompatible carrier matrix. Moreover, the carrier matrix can be either a homogeneous matrix or a heterogeneous matrix, as desired.

In one embodiment, the carrier matrix can be hydrophilic in nature. This can be preferred when utilizing the invention in an aqueous-based system, for example in a clinical setting, as a hydrophilic matrix can be less likely to provoke an immunosuppression response to the matrix by a patient. This is not a requirement of the invention, however, and in other embodiments, the carrier matrix can be a hydrophobic polymeric matrix.

In one embodiment of the invention, the carrier matrix can be a hydrogel. For instance, the carrier matrix can be a biocompatible hydrogel. Hydrogels are herein defined to include polymeric matrices that can be highly hydrated while maintaining structural stability. Suitable hydrogel matrices can include un-crosslinked and crosslinked hydrogels. In addition, crosslinked hydrogel carrier matrices of the invention can optionally include hydrolyzable portions, such that the matrix can be degradable when utilized in an aqueous environment. For example, in one embodiment, the carrier matrix can include a cross-linked hydrogel including a hydrolyzable cross-linking agent, such as polylactic acid, and can be degradable in an aqueous environment.

Hydrogel carrier matrices of the present invention can include natural polymers such as glycosaminoglycans, polysaccharides, proteins, and the like, as well as synthetic polymers, as are generally known in the art. A non-limiting list of hydrophilic polymeric materials that can be utilized in forming hydrogels of the present invention can include dextran, hyaluronic acid, chitin, heparin, collagen, elastin, keratin, albumin, polymers and copolymers of lactic acid, glycolic acid, carboxymethyl cellulose, polyacrylates, polymethacrylates, epoxides, silicones, polyols such as polypropylene glycol, polyvinyl alcohol and polyethylene glycol and their derivatives, alginates such as sodium alginate or crosslinked alginate gum, polycaprolactone, polyanhydride, pectin, gelatin, crosslinked proteins peptides and polysaccharides, and the like.

Hydrogel matrices of the present invention can be formed according to any method as is generally known in the art. For instance, the hydrogel can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, the hydrogel can be polymerized in the presence of an initiator. For example, in one embodiment, the hydrogel can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

The components of the carrier matrix can also be designed so as to provide a self-assembling carrier matrix. For example, in one embodiment, a hydrogel precursor can be administered to a patient, and the hydrogel matrix can self-assemble at physiological conditions following administration of the precursor. For instance, the hydrogel precursor can include self-assembling biopolymers such as collagens, laminins, pro-elastin peptides, and the like. Optionally, a self-assembling hydrogel precursor can include synthetic polymers that can array themselves according to domains, as is generally known in the art. For example, hydrophilic, relatively charge-neutral synthetic polypeptides such as polyglycine or polylysine can be modified to function in this capacity. Polypeptides can be crosslinked by using carboxy-activating crosslinking agents such as water-soluble carbodiimides. Such cross-linking agents can be used to attach self-assembling proteins or other self-assembling macromolecules to the polypeptides. One example of this approach includes formation of a carbodiimide linkage of collagen or laminin with polylysine. Other hydroxylated entities can be linked in a similar manner. For example, in one embodiment, polyvinyl alcohol can be linked with polypeptides using an epoxy-activation approach or crosslinked via polymerizable methacrylate groups along its side chains, as is known in the art.

In another embodiment, a self-assembling hydrogel can be generated by use of precursors that have been derivatized to contain favorably reactive groups. For example, a hydrogel of this type could be assembled using a first precursor derivatized with a particular reactive moiety and a second precursor derivatized with or comprising a second moiety that can preferentially react with the first moiety on the first precursor. Likewise, other such hydrogels could be generated using such reactive pairs wherein the two moieties that react to form the bond are each conjugated to the same or a different type of polymer. For example, the pairs can be antibody-antigen pairs or avidin-biotin (e.g. streptavidin-biotin).

In other embodiments the carrier matrix need not be a self-assembling matrix. For example, in other embodiments a hydrogel matrix for use in vivo can be administered to a patient according to a suitable administration method (e.g., orally or percutaneously) following assembly of the hydrogel. In other embodiments of the invention, the disclosed systems can be utilized in ex vivo applications, for example in tissue engineering applications, and as such, the carrier matrix of the invention need not be a self-assembling matrix.

In one embodiment of the present invention, the carrier matrix can be a highly porous matrix. For example, a hydrogel can be formed with mesh size, $\xi$, much larger than the size of the biologically active agent to be carried and delivered by the system. More specifically, the initial mesh size of a degradable matrix, or the constant mesh size of a non-degradable matrix, can be considerably larger than the size of the biologically active agent to be carried by and delivered from the matrix. For example, in one embodiment, the mesh size of a hydrogel carrier can be large enough to allow free diffusion of a macromolecular protein therapeutic agent through the hydrogel. In one particular embodiment, the carrier matrix can be formed to have a mesh size, $\xi$, between about 5 and about 50 nm.

In one embodiment, the carrier matrix can be formed to have a mesh size that is smaller than the ligand/drug complex and yet larger than the drug itself. According to this particular embodiment, the drug can be held within the matrix through purely physical constraints as long as it is associated with the ligand, and can become free to diffuse through the matrix upon dissociation of the drug from the ligand. Any particular mesh size is not a requirement of the present invention, however, and the selection of any particular mesh size can generally depend at least in part upon the size of the biologically active materials to be delivered by the system.

In accord with the present invention, the carrier matrices can include a ligand within the matrix. In particular, the ligand included in the matrix can have a pre-selected affinity for a biologically active agent that can be carried by and delivered from the matrix. Through inclusion in the carrier matrix of the particular ligand at a predetermined loading concentration, it has been discovered that the release rate of the agent from the matrix can be controlled. In addition, it has been discovered that through association of the agent with a chosen ligand, the agent can be held in a protective complex throughout the delivery process such that detrimental reaction of the agent with the carrier matrix can be avoided. In one embodiment, the predetermined affinity between the ligand and releasable agent can be sensitive to external conditions such as temperature or pH that could allow stimuli-sensitive release of the agent. For example, a system with pH-sensitive binding affinity may be designed for drug delivery from the matrix into an environment at high pH values, e.g., the intestines.

As used herein, the term 'ligand' can include any molecular group that can be included within the matrix that can have a specific or psuedo-specific reversible, non-covalent binding affinity for a biologically active agent to be carried by and delivered from the disclosed system. In addition, while the ligands of the disclosed system can, in one embodiment, be covalently bound within the matrix, this is not a requirement of the invention. For example, in other embodiments, the ligands can be held within the matrix through hydrogen or ionic bonding, though the bond strength of the bond holding the ligand in the matrix can, in one embodiment, be greater than that of the ligand/drug complex. In another embodiment the ligand, a ligand-protein complex, or a poly(ligand-protein) complex may be physically entrapped within the network due merely to its size, with no bonding between the complex and the polymeric matrix. In another embodiment the ligand may be immobilized onto a separate network as part of a (semi)interpenetrating network (IPN).

In one embodiment, the ligand need not be bound or otherwise held within the matrix itself. According to this embodiment, the ligand may serve merely as a protective associate to the agent to be delivered. For instance, in this particular embodiment, the agent can be held in a ligand/agent reversible association and thereby prevented from reaction with matrix components. Thus, due to the protective nature of the complex formation in this embodiment, an increase in drug delivery efficiency can be brought about as compared to systems in which the drug or agent is unprotected. In these unprotected systems, a large amount of the agent can be irretrievably bound or otherwise lose therapeutic value due to reaction with the carrier itself or with carrier components during matrix formation and/or drug delivery.

The methods and systems of the present invention recognize that the rate of release of a biologically active agent from the carrier matrix can depend not only upon the rate of diffusion of the agent through the matrix, which has been recognized and utilized in the past, but can also depend upon the equilibrium characteristics of the drug/ligand complex within the carrier matrix. This invention thus pertains in one embodiment to the fabrication and use of drug-delivery systems in which the drug release rates are not merely diffusion controlled. This characteristic allows release profiles other than those resembling first-order kinetic behavior to be designed. It also permits the release rate and cumulative release of the drug to be independent of the size and shape of the delivery matrix. In particular, according to the present invention, the percentage of the drug held in the matrix in the drug/ligand complex during the delivery period and hence the percentage of the drug available to be delivered from the system to a biological system can be controlled through design and/or selection of the type and loading concentration of the ligand irregardless of matrix shape and/or permeability.

The affinity that a ligand has for a biologically active agent can be described by the apparent equilibrium dissociation constant, $K_D$. In one particular example, $$K_D = \frac{[C_L][C_D]}{[C_{LD}]}$$

where $C_L$ is the concentration of the free ligand in the matrix $C_D$ is the concentration of the free drug in the matrix and $C_{LD}$ is the concentration of the ligand/drug complex in the matrix.

Of course, as is generally known in the art, $K_D$ may be expressed in other more complex forms for particular drug-ligand combinations.

Simple material balances of the drug and ligand concentrations within the matrix can be expressed as:

$C_{LT} = C_L + C_{LD}$ and $C_{DT} = C_D + C_{LD}$ where $C_L$, $C_D$, and $C_{LD}$ are as defined above and $C_{LT}$ is the total concentration of the ligand in the matrix and $C_{DT}$ is the total concentration of the drug in the matrix Thus, through combination of these equations, the following quantitative relationship can be obtained for a system with the simple binding interactions and $K_D$ described above:

$$K_D = \frac{(C_{LT} - C_{LD})(C_{DT} - C_{LD})}{C_{LD}}$$

This equation can be solved for the concentration of ligand-drug complex ($C_{LD}$), which can be readily expressed in the form of percent drug bound by dividing it with the total concentration of drug ($C_{DT}$) inside the matrix:

$$\% \text{ Drug Bound} = \left(\frac{C_{LD}}{C_{DT}}\right) \times 100 = 50 \times \left(b - \sqrt{b^2 - 4\frac{C_{LT}}{C_{DT}}}\right)$$

where $$b = \left(1 + \frac{C_{LT}}{C_{DT}} + \frac{K_D}{C_{DT}}\right)$$

Thus, the percentage of drug bound at any time depends primarily upon three parameters: (i) the strength of the interaction between the ligand and the drug ($K_D$), (ii) the total concentration of the drug present in the network ($C_{DT}$), and (iii) the ratio of the total concentration of the ligand to the total concentration of the drug ($C_{LT}/C_{DT}$). During the release process from a non-degradable or substantially non-degradable matrix, the concentrations of total drug ($C_{DT}$), unbound drug ($C_D$) and bound drug ($C_{LD}$) present in the matrix can change with time while the total concentration of the ligand ($C_{LT}$) can remain the same. (For purposes of this disclosure, the term 'substantially non-degradable' is herein defined to mean that the degradation rate of the matrix is at least one order of magnitude less than the delivery rate of the drug from the matrix.)

During release of the agent from a degradable matrix, $C_{LT}$ can vary with time, but this variation can be a known relationship. In this case, $C_{LT}$ will decrease at a rate commensurate with the rate of matrix degradation, which is a known quantity. Thus, in either case, while the percent drug bound is a function of time, it can be affected and controlled by controlling the other known parameters, $K_D$, $C_{LT}$, and matrix degradation rate.

A numerical model using a finite-difference method to simulate the release behavior of various model large macromolecular protein agents from a slab-shaped hydrogel matrix has been used to examine the effect of the ligand concentration and dissociation constant parameters on the release rate of a solute from the matrix. The model, in addition to accounting for the strength of the ligand/drug interaction and the amount of ligand present in the network, also accounts or the effects of mesh size and drug size chosen, as well as diffusion characteristics of the free drug through the matrix. It should be understood, however, that, while the model systems discussed below have been developed as systems designed for delivery of macromolecular protein materials, the methods and systems of the present invention are equally suitable to smaller biologically active agents and/or networks of proportionally smaller mesh sizes.

For the discussed model calculations, the mesh size or pore size of the homogeneous polymer network was determined using the equations described by Canal and Peppas (T. Canal and N. A. Peppas, 'Correlation between mesh size and equilibrium degree of swelling of polymeric networks', J. Biomed. Mater. Res. 23(10) (1989) 1183-1193, which is incorporated herein by reference), and in general was at least twice as large as the average diameter of the material to be delivered from the system (i.e., greater than about 5 nm). An estimation of the drug diffusivity in dilute aqueous solution was calculated using the Stokes-Einstein equation, and the diffusivity within the crosslinked hydrogel network was related to this diffusivity in solution by the free volume approach developed by Lustig and Peppas (Lustig S. R., Peppas N. A., Solute diffusion in swollen membranes. IX. Scaling laws for solute diffusion in gels', *J. Appl. Polym. Sci.*, 36(4) (1988) 735-747, which is incorporated herein by reference). In addition, the model assumed that all ligand present in the gel was bound completely to the network throughout the release time, and the drug molecules in the free state were assumed to diffuse freely, while the free ligand and bound ligand/drug complex were assumed to be immobilized and not diffuse. Two boundary conditions were used to solve the model equations: (i) the concentration of diffusible species (i.e., free drug) outside the gel was assumed to be zero (infinite sink assumption) and (ii) diffusion was symmetric about the center of the gel. A high aspect ratio was imposed on the gel and thus one-dimensional diffusion was assumed to take place according to Fick's law.

FIG. 1 shows the predicted effect of $K_D$ on the percent drug binding to a non-degradable or substantially non-degradable matrix. Referring to FIG. 1, as the dissociation constant ($K_D$) decreases, the concentration of the bound, non-diffusible drug increases and the concentration of freely diffusible, unbound drug ($C_D$) decreases. As can be seen, the effect can be broadly classified into three regimes: (regime I) low $K_D$ values where the binding strength is very high and most of the drug molecules are immobilized onto the ligands at any given time; (regime II) high $K_D$ values where the strength of binding is too low to immobilize any significant portion of the drug molecules; and (regime II) intermediate $K_D$ values where the percentage of drug molecules bound to the network increases with an increase in the strength of interaction (i.e. decrease in $K_D$) in a sigmoidal fashion. Particular values defining regimes I, II, and III for any particular system can vary depending upon the other system parameters, specifically, $C_{DT}$ and $C_{LT}/C_{DT}$. For example, in one exemplary embodiment, regime I can include those systems with $K_D$ values lower than about 1.0E-5 mM, regime III can include those systems with $K_D$ values between about 1.0E-5 mM and about 1.0E+1 mM, and regime II can include those systems with $K_D$ values greater than about 1.0E+1 mM.

Figure 2:
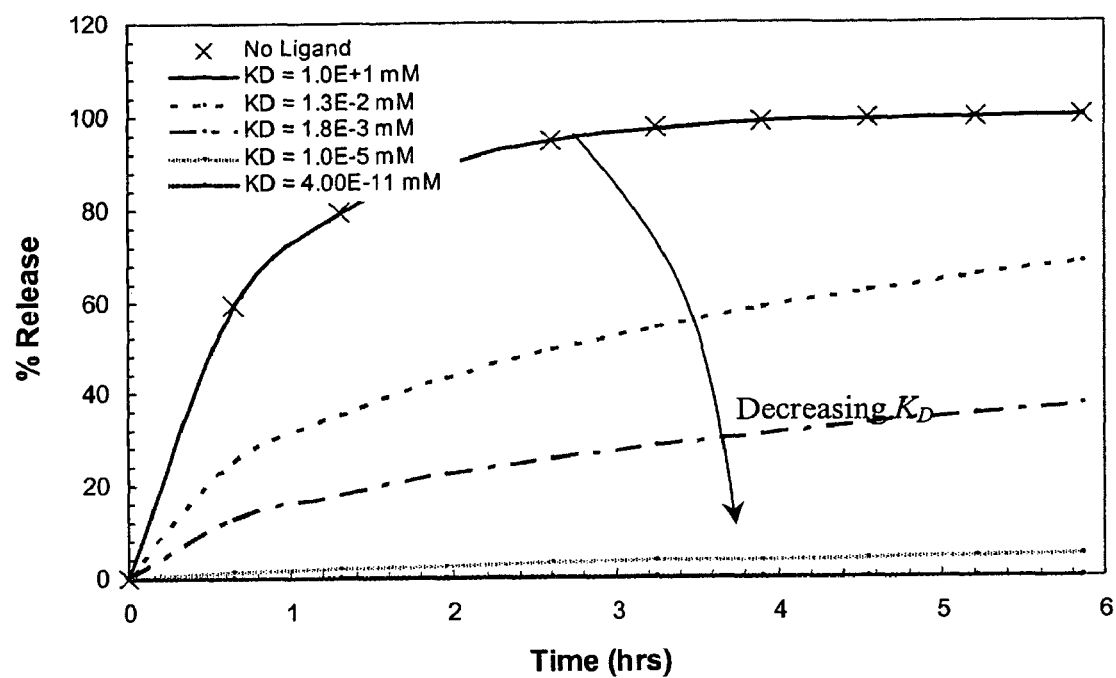
FIG. 2 shows the predicted effect of decreasing $K_D$ on the release rate of materials from otherwise identical carrier matrices.

Thus, for the system described in FIG. 1, at $K_D$ values below about 1.0E+1 mM, a decrease in $K_D$ decreases the amount of freely diffusible drug inside the matrix. This result leads to a decrease in the concentration gradient of diffusible drug between the matrix and the environment surrounding the matrix, resulting in slower drug release rates, as can be seen by reference to FIG. 2.

In regime I of FIG. 1, where the binding strength is high (i.e., $K_D$ less than about 1.0E-5 mM), a slight change in $K_D$ can lead to a large variation in the overall time for 100% release of drug. According to one embodiment of the present invention, ligands can be selected for the disclosed systems that exhibit a relatively low $K_D$ with the agent to be delivered from the matrix so as to beneficially take advantage of the sensitivity and high binding capabilities of ligand/agent complexes in this regime. For example, in one embodiment, a ligand can be selected or manufactured that has a $K_D$ with the agent to be delivered from the matrix of less than about 1.0E-5 mM. In one embodiment, the disclosed systems can include a ligand that exhibits a $K_D$ with the agent to be delivered from the matrix of between about 1.0E-5 mM and about 1.0E-9 mM. According to one embodiment, the release rate of the agent from the matrix can be almost entirely controlled by the equilibrium conditions of the complex, as at suitably high ligand concentrations most of the drug in the matrix at any time can be held in the form of the ligand/drug complex and thus prevented from diffusing out of the matrix.

Many ligand-drug combinations of various $K_D$ values are readily available from the field of affinity chromatography. Thus, according to one embodiment of the present invention, an existing ligand for a particular bioactive agent can be selected and incorporated into the carrier matrix according to the known $K_D$ of the known ligand/agent complex. For example, a metal-chelating agent such as imino(diacetic acid) can be selected that can exhibit the predetermined desired reversible affinity for a protein bearing an exposed histidine amino acid in its native sequence or a poly-histidine tag engineered onto either protein-chain terminus.

Optionally, a ligand can be manufactured to exhibit a particular $K_D$ with an agent. In particular, according to one embodiment of the present invention, a ligand for a biologically active agent to be delivered from the system can be designed to exhibit a particular affinity for that agent as well as containing a particular derivatization that can be used for incorporation of the ligand into the carrier matrix. For example, a ligand can be particularly designed, such as through utilization of a bacterial phage display or another combinatorial synthesis technique, as is generally known in the art, so as to exhibit a target $K_D$ value with the agent to be delivered from the carrier matrix. In addition, a pre-designed ligand can include a particular moiety to covalently or otherwise bind the ligand within the matrix. The ligand can then be incorporated within the carrier matrix at the designated concentration level to provide a system exhibiting a predetermined release rate of the agent from the ligand-functionalized carrier.

It should be understood, however, that while particularly designed and constructed artificial ligands can be advantageously utilized in one preferred embodiment of the present invention, this is not a requirement of the invention. In other embodiments, naturally occurring ligands can be utilized. For example, naturally occurring ligands from a protein/ligand pair can be incorporated within the carrier matrix and utilized to carry and deliver the protein of the pair to a biological system. Optionally, a chimera and/or a fragment of a naturally occurring ligand can be incorporated in the matrix to carry the biologically active agent. For example, in one embodiment the naturally occurring ligand, or a fragment thereof, can be derivatized at a sight suitably distant from the segment where the ligand can bind with the biologically active agent in order to be incorporated into the matrix via the derivatization segment. According to this embodiment of the invention, the $K_D$ of the ligand/protein binding pair in the matrix can be engineered to be similar or even identical to that of the pair in its natural setting.

The predetermination of the concentration of ligand contained within the carrier matrix can be utilized in cooperation with the dissociation constant value to affect the delivery rate of the agent from the system. In particular, for a chosen drug-ligand combination at a given loading concentration of the drug (i.e., $K_D$ and $C_{DT}$ are fixed) the amount of drug initially bound to the ligands can increase with an increase in total ligand concentration ($C_{LT}$). Thus, increasing the number of ligands bound within the carrier matrix can immobilize more molecules in order to maintain binding equilibrium, resulting in a higher binding percentage and a slower drug delivery rate. However, this effect is prominent only when the $K_D$ value is low enough to see an appreciable interaction between the ligand and the bioactive agent molecules (e.g., $K_D$ value is present in regime I or II).

Figure 3:
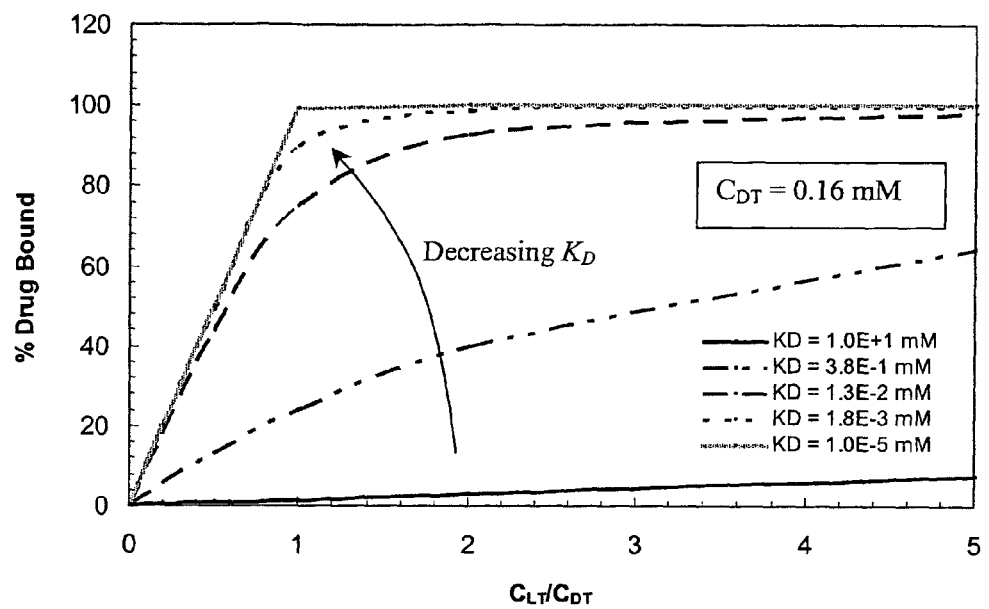
FIG. 3 shows the predicted effect of changing the total ligand concentration on the percent of drug initially bound to the matrix at various values of $K_D$.
Figure 4:
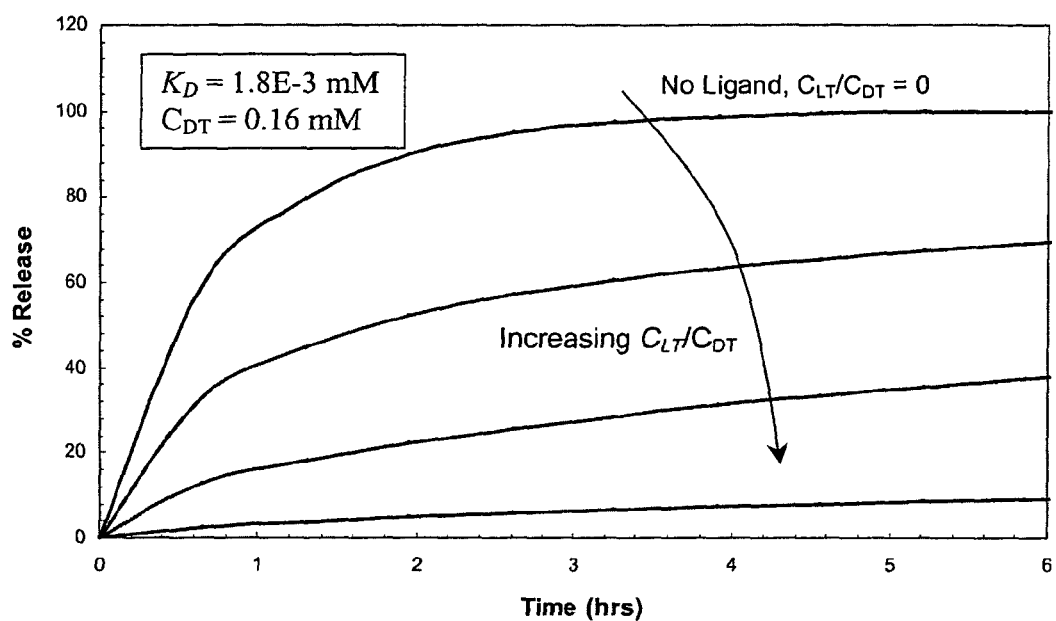
FIG. 4 illustrates the predicted change in drug release rate for various concentrations of total ligand at a constant $K_D$.

Referring to FIG. 3, illustrated is the effect of changing the total ligand concentration on the percentage of drug bound to the ligand for systems of various affinities. As can be seen, for $K_D$ values greater than 1.0E+1 mM, the effect of increasing the ligand concentration on the amount of ligand-drug binding is negligible while for drug/ligand combinations with $K_D$ values falling in regimes I and III, the percentage of drug molecules binding to the network increases with an increase in $C_{LT}/C_{DT}$ ratio for a given $C_{DT}$ (i.e., an increase in $C_{LT}$). However, it is noteworthy that at $K_D$ values less than 1.0E-5 mM (regime I), drug molecules can be immobilized in a stoichiometric ratio to the number of ligands due to the strong affinity between the two. As expected, this increase in percent binding leads to a decrease in the drug release rates. FIG. 4 illustrates the predicted decrease in solute release rates as the $C_{LT}/C_{DT}$ ratio is increased for a system in which the $K_D$ value falls in regime III (i.e., between about 1.0E-5 mM and about 1.0E+1 mM) at a $C_{DT}$ of 0.16 mM. Obviously, the particular concentration of drug to be delivered from the disclosed systems, and hence a possible range for an absolute value of the ligand concentration to be incorporated into the disclosed matrices can vary widely depending upon the type of drug, the drug delivery method (e.g., ingestion vs. subdermal or muscular injection), the application (e.g., in vivo vs. in vitro), the weight of the patient, along with many other different parameters. Thus, the range of ligand concentration that can be incorporated into the disclosed systems has been described throughout much of this discussion in terms of the concentration of the drug to be delivered by the system (i.e., $C_{LT}/C_{DT}$). For instance, in one embodiment, the ratio of the ligand concentration to the drug concentration loaded into the disclosed systems can be between about 1:10 and about 10:1. In another embodiment, the ratio of the concentration of ligand to drug incorporated into the carrier matrix can be between about 1:5 and about 2:1.

Thus, according to one embodiment of the present invention, a drug delivery system can be designed by choosing or manufacturing a ligand for a particular bioactive agent to be delivered from the system in which the ligand-agent association exhibits a particular, predetermined $K_D$ at equilibrium, and tailoring the release profile by incorporating a particular, predetermined concentration of ligand ($C_{LT}$) into the matrix for a given amount of drug ($C_{DT}$) at t=0 (i.e. prior to any diffusion of material from the system) to obtain the particular release rate desired.

According to another embodiment, however, the converse method can optionally be utilized in designing the disclosed systems. That is, a system incorporating a known concentration of ligands can be designed, and the release profile of the drug can be tailored by designing a synthetic ligand or choosing a naturally occurring ligand that has a particular $K_D$ with the drug to be delivered. Of course, a combination of the two approaches can be used as well.

Figure 5:
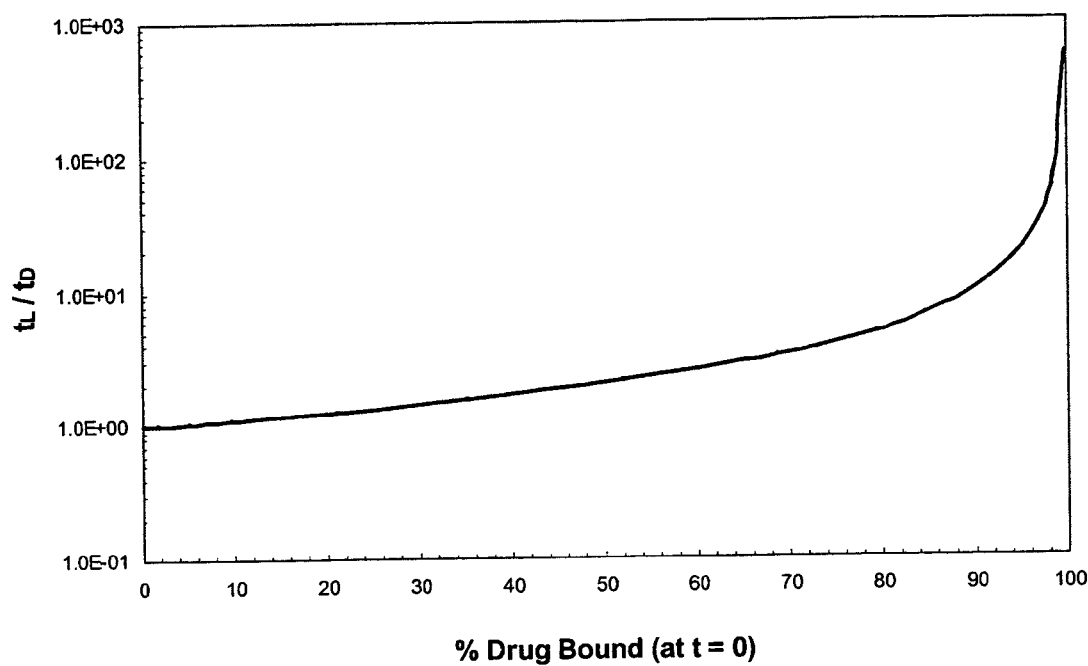
FIG. 5 illustrates the combined effects of the examined drug release parameters on the release rate of a drug from a non-degradable or substantially non-degradable hydrogel matrix of any given thickness and permeability.
Figure 6:
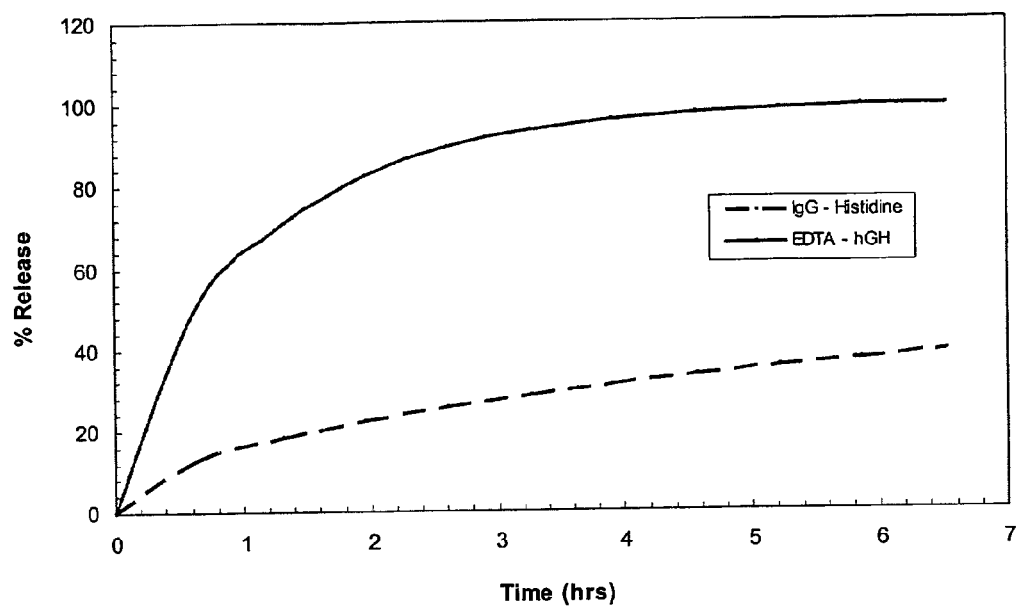
FIG. 6 illustrates the predicted release rates of two different bioactive agents from a single carrier matrix according to one embodiment of the invention.

FIG. 5 illustrates the combined effects of the drug release parameters $K_D$ and $C_{LT}/C_{DT}$ on the release rate of a drug from a non-degradable or substantially non-degradable hydrogel matrix of any given thickness and permeability via their impact on the percent of solute (drug) initially immobilized with the ligand. In obtaining FIG. 5, simulations were performed to estimate the time for 90% release of a macromolecular protein drug from non-degradable or substantially non-degradable hydrogel matrices of various thicknesses and permeabilities with varied combinations of $K_D$ and $C_{LT}/C_{DT}$. The time for release of 90% of the material from a system with no ligand (i.e., $C_{LT}=0$) is represented by $t_D$ while the time for 90% of the material to be released from a similar system but incorporated with ligands is represented by $t_L$. The percentage of drug initially bound to the network was determined for each of these cases and plotted against the ($t_L/t_D$) ratio. Thus, for a given matrix, $t_D$ will be fixed and $t_L$ varies with $K_D$ and $C_{LT}/C_{DT}$.

As can be seen, an increase in the percentage of drug bound to the network at t=0 increases the time for drug release (i.e., $t_L$ increases). In systems with no ligands or with ligands exhibiting very weak interaction with the releasable drug, the time for release can depend solely on the diffusion coefficient of the drug within the gel. The dimensionless parameter ($t_L/t_D$) for these systems where the rate of release is completely diffusion controlled would be unity (i.e., $t_L=t_D$). At the other end of the binding spectrum, the rate of release can be controlled by the equilibrium state of the ligand/drug complex, and the release time ($t_L$) becomes very sensitive to the percent drug bound at percentages approaching 100% (i.e., high $C_{LT}/C_{DT}$ and/or low $K_D$). This result is expected since complete (100%) binding of the drug leads to an infinite amount of time for release.

It should be understood that while the above discussion in general and FIG. 5 in particular is directed toward a non-degradable or substantially non-degradable network, the disclosed methods and systems can additionally be utilized with degradable networks. In particular, when considering degradable networks, the degradation rate of the matrix can be incorporated as an additional control parameter to control the release rate of the biologically active material from the matrix. For instance, when considering a degradable network, the effect of the degradation of the matrix can decrease the total concentration of the ligand over time in a known fashion (since the degradation rate of the matrix is known) and can lead to a release profile that deviates from first-order behavior. For example, absolute release rate of the drug from the matrix may remain constant over time (zero-order release profile) or even increase with time.

Beneficially, the disclosed invention can be utilized for delivery of practically any unmodified biologically active agents. For example, the disclosed systems can be utilized to deliver pharmaceutically useful drugs in the treatment or prevention of disease. In addition, the systems can be utilized to deliver diagnostic agents within a system, including imaging agents, as well as growth and nutrient agents, to encourage the healthy development of a biological system, including the development of individual cells in tissue engineering applications. As such, the terms "drug" and "biologically active agent" are often used interchangeably in this disclosure though the term "biologically active agent" is not intended to be limited to known drugs or therapeutic agents. A non-limiting list of exemplary types of materials that can be considered as biologically active agents in the disclosed invention can include, for instance, proteins, peptides, oligonucleotides, polysaccharide, and biologically active small molecules.

Due to the beneficial design of the present invention, the ligand itself and the incorporated ligand concentration can be selected or designed for the disclosed systems based upon the characteristics of the particular agent to be delivered. In the past, the opposite approach was taken. That is, in the past, a carrier matrix was first designed, and then a drug to be delivered by the matrix would be altered as necessary to be carried by the matrix. For example, in the past, a drug could be altered such as through derivatization or alteration in size (e.g., delivering only a particular polypeptide sequence of a larger protein therapeutic) so as to chemically and physically cooperate with the carrier. Unfortunately, this approach cannot work with many drugs, and particularly with many larger, macromolecular protein therapeutics due to, for example, size constraints and deactivation of the therapeutics due to the alteration of the materials. In the present system, in contrast, the carrier can be designed with the unmodified agent in mind, rather than the other way around. For example, an artificial ligand can be selected or constructed according to the particular $K_D$ desired for the unmodified drug. As such, the disclosed system can be utilized for delivery of unmodified protein therapeutics for treatment of multiple diseases including, for example, autoimmune diseases such as rheumatoid arthritis, ulcerative colitis, Crohn's disease, and AIDS; chronic diseases such as cystic fibrosis, muscular dystrophy, Parkinson's Disease, dwarfism, anemia, and diabetes; viral infectious diseases such as hepatitis; and cancer.

In addition, due to the predetermined affinity of the chosen ligand for the agent, the disclosed methods and systems can also be utilized to beneficially protect the agents to be carried by and delivered from the carrier matrices from possible side reactions prior to delivery. In particular, according to one embodiment of the invention, the agent/ligand complex can be established prior to or during incorporation of the ligand into the matrix or prior to possible contact between the biologically active agent and other materials with which the agent could react in a detrimental fashion. For example, the protective association can be established so as to hold the agent in an unreactive state and thus protect the agent from side reaction with the components forming the matrix, from side reaction with the formed matrix itself, as well as from side reaction with certain materials the loaded matrix may encounter prior to delivery of the agent from the matrix (e.g., active materials within a biological system that has received the loaded matrix). According to this embodiment, the agent can be protected from side reactions until the agent is released from the ligand according to the control mechanism based upon the predetermined release profile. For example, in those embodiments wherein $K_D$ of the agent/ligand complex falls into Regime I, the agent can be particularly well protected from possible side-reactions prior to delivery due to the high affinity of the agent for the ligand held in the matrix.

Thus according to one aspect of the present invention, systems and methods are provided that can protect an underivatized or unaltered biologically active agent from side reactions, and in particular, from side reactions that could effect the efficacy of the agent, during formation and loading of a carrier matrix as well as during utilization of the matrix up to and including the time of delivery of the drug from the ligand and/or from the matrix to a target tissue. In particular, the agents can be protected from side reactions due to association with the chosen ligand, wherein $K_D$ of the association is predetermined as is the loading concentration of the ligand so as to define a particular release profile for the drug from the ligand. Following release of the drug from the ligand according to the predetermined release profile, the drug can be available in the unaltered, unassociated state for interaction with a target cell or tissue.

In one embodiment, the present invention is directed to systems and methods that can incorporate both aspects of the disclosed invention. That is, the biologically active agent to be delivered can be protected from side reactions due to the association of the biologically active agent with the ligand. In addition, in this embodiment, the ligand can also be incorporated into the carrier matrix in a substantially permanent fashion (e.g., the ligand can be bound to or held in the matrix with a much stronger affinity than that forming the ligand/drug complex). According to this embodiment, the disclosed invention can provide a predetermined release rate profile of the drug from the carrier matrix itself in addition to providing protection of the underivatized drug from side-reactions prior to release.

In one embodiment, the systems and methods of the present invention can be utilized to control the drug delivery rate of materials from carrier matrices having large mesh sizes. In particular, as the type and concentration of ligand loaded into the matrix can be utilized to control the release rate of the drug carried by the matrix, other, previously utilized control parameters, such as mesh size, for example, which have been utilized to control the diffusion rate of the drug from the matrix, need no longer be of primary importance. Utilizing the disclosed systems and methods, delayed and controlled release rates can be obtained even with highly porous networks (large $\xi$) through selection of ligand concentration and through selection of a system exhibiting a particular ligand/drug affinity.

In addition, unlike traditional encapsulating hydrogels which offer limited control over the release rate of a drug from the hydrogel at only relatively small mesh sizes (e.g., mesh size near the average drug size), systems of the present invention can offer precise control over the release rates of drugs over a wide range of desired release rates. In particular, the release of macro-molecules from homogeneous matrices with extremely large mesh sizes or heterogeneous matrices with large pores can be controlled leading to sustained release of these molecules over therapeutically relevant timescales. In addition, in traditional gels, decreasing the mesh size to obtain sustained release makes the gels compact and increases the hydrophobicity of the network. This increase in hydrophobicity of the system can destroy the advantageous stealth character offered by highly biocompatible matrices such as hydrophilic PEG systems and activate an immune response towards the gel.

According to one embodiment of the present invention, the disclosed systems and methods can be beneficially utilized for release of multiple drugs at independently controlled rates from a single carrier matrix. For example, according to this particular embodiment, two or more drugs can be immobilized into a single carrier matrix by incorporating the same different ligands that show specific interactions with the corresponding drug molecules. Release of each drug can then be determined and controlled by the strength of the specific drug-ligand interaction and the concentration of ligand displaying that interaction, and release of the different agents can thus be controlled independently.

FIG. 6 illustrates the varying release rates of two different bioactive agents from a single carrier matrix according to theoretical predictions based on this particular embodiment of the invention. In particular, FIG. 6 illustrates the predicted release rates of materials from a system that is incorporated with two ligands, Zn-ethylenediamine tetraacetic acid (Zn-EDTA) and histidine, which exhibit specific interactions with human growth hormone (hGH) and immunoglobulin G (IgG), respectively. According to the present invention, release rates of these protein therapeutics can be controlled independently based on the amounts of ligands and the strengths of interaction between corresponding ligand-drug combinations. As can be seen in the Figure, due primarily to the weak interaction between hGH and Zn-EDTA ($K_D$=3.8E-1 mM) compared to the interaction between IgG and histidine ($K_D$=1.8E-3 mM) as well as the size difference between the drug molecules, the release of hGH is predicted to occur significantly faster from the matrix than does IgG.

This method can be particularly effective for delivering multiple specialized growth factors to cells encapsulated within highly porous networks in a way that mimics the native extracellular matrix, i.e., in tissue engineering applications.

According to yet another embodiment of the present invention, systems can be designed exhibiting a bi-phasic release behavior. In particular, a bi-phasic release behavior can be designed through utilization of $C_{LT}/C_{DT}$ ratio less than unity. For purposes of this disclosure, bi-phasic release behavior is herein defined as a release that occurs in two distinct phases including different release rates in each phase.

Figure 7:
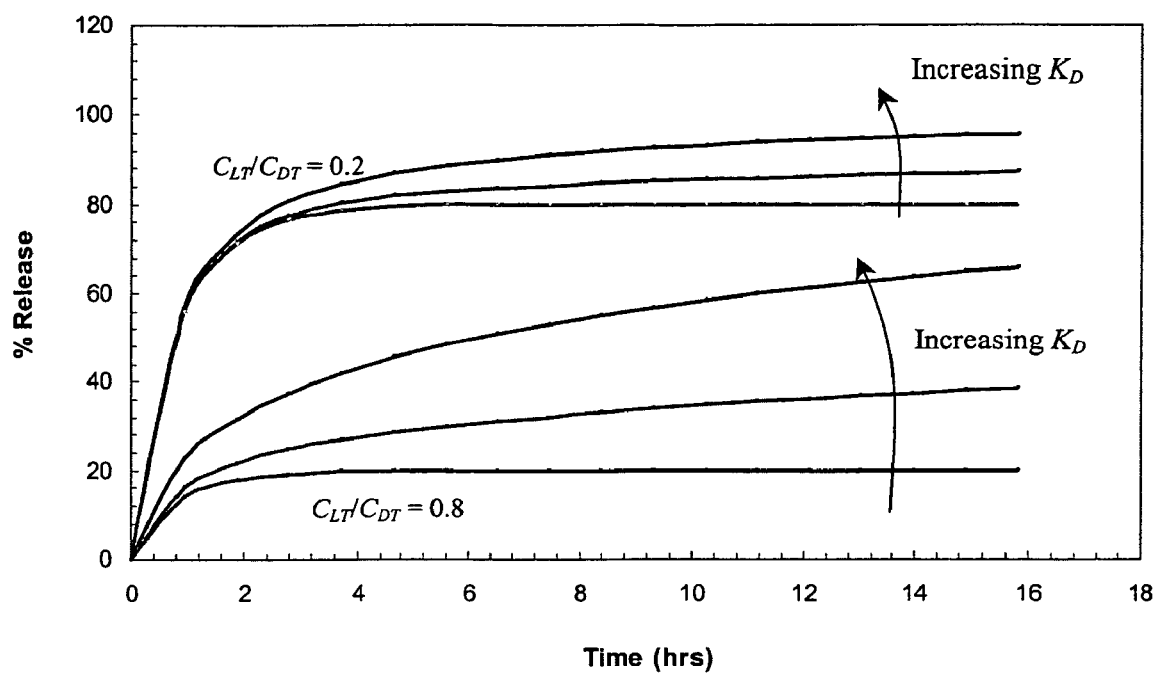
FIG. 7 illustrates one embodiment of the present invention exhibiting bi-phasic release behavior of biologically active agents from a carrier matrix.

FIG. 7 illustrates one particular embodiment of the present invention exhibiting bi-phasic release behavior. According to this particular embodiment, the amount of drug that is released during the first phase can be controlled by varying the $C_{LT}/C_{DT}$ ratio, while the rate of release during the second phase can be tailored by varying $K_D$. Biphasic behavior can become more prominent as the interaction force between ligand and drug increases (i.e., as $K_D$ decreases). In particular, during the first phase of release, as the $C_{LT}/C_{DT}$ ratio decreases, the amount of drug immobilized onto the network decreases, as described above. This can lead to a faster overall release due to a higher amount of free drug (i.e., higher concentration gradient). This first phase of the release is thus primarily diffusion controlled while the second phase of the release is controlled by the reaction equilibrium maintained between the ligand and drug.

The carrier matrices of the present invention can include additional materials as well, in addition to the drug/ligand complexes of the present invention. For example, in one embodiment, the carrier matrix can include live cells or agglomerations of live cells, for instance in tissue engineering applications. According to this embodiment, the biologically active materials to be delivered by the system can include growth and development factors for delivery to the living cells held within the matrix itself. In addition, in this particular embodiment, the matrix can include cell membrane receptor ligands within the hydrogel that can stimulate adhesion, spreading, and growth of cells. As such the matrix, or in this case, the tissue engineering scaffold, can more closely resemble the extracellular matrix of a living organism, and thus encourage the healthy development of the cells held in the matrix.

Other materials that can be included in the matrix can include materials for targeting the matrix to particular cell or tissue types such as during in vivo utilization of the materials. For example, according to one embodiment of the invention, the matrix can include one member of a particular protein-ligand pair. In particular, either the protein or the ligand of a protein-ligand pair can be present at the exterior surface of the carrier matrix. Accordingly, the matrix can specifically associate with a cell or tissue that comprises the other member of the protein-ligand pair. Similarly, a cell or tissue which includes either the protein or the ligand of the protein-ligand pair at the exterior surface of the material can specifically associate with a carrier matrix that comprises the other member of the protein-ligand pair. Thus, the carrier matrix can be targeted to a particular type of cell or tissue or vice versa, and the drug carried by the matrix can be delivered from the matrix while the matrix is associated with that particular cell or tissue.

The disclosed invention may be better understood by reference to the examples, below.

Example 1

Two macromolecular solutes, bovine serum albumin (BSA) and immunoglobulin G (IgG), were released from PEG 3400 DA (di-acrylated poly(ethylene glycol)) gels fabricated under identical conditions. The gels were formed by polymerization of a 10 wt % PEG 3400 DA solution in buffer. Once equilibrated in a large excess of buffer, the volumetric swelling ratios of the polymerized release matrices were observed to remain identical in all the cases indicating no degradation. The mesh size of the gels was estimated to be 140 Å based on the average measured mass swelling ratios of the gels ($Q_m$=13.2±1.7).

Both BSA and IgG protein molecules chosen were smaller than the mesh size of the 10 wt % PEG 3400 DA gels and, thus, were expected to readily diffuse out of the hydrogel driven by a concentration gradient. The method of release of protein in this example was thus diffusion controlled and depended solely on the relative sizes of the network mesh ($\xi$) and encapsulated protein molecules ($r_s$).

Figure 8:
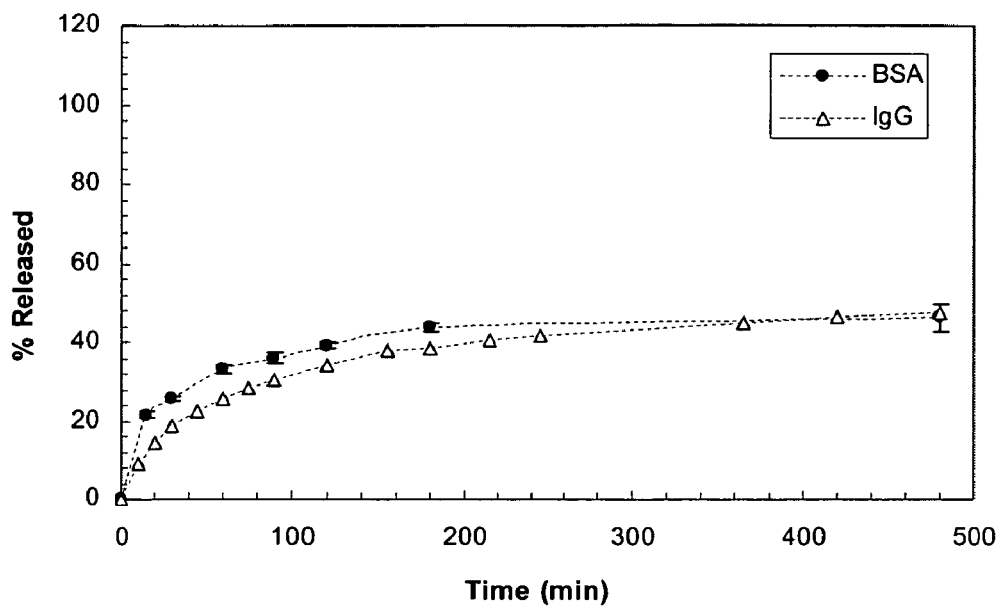
FIG. 8 graphically illustrates the cumulative percentage release of bovine serum albumin (BSA) and Immunoglobulin G (IgG) from 10 wt % PEG 3400 DA gel with a 5 wt % drug loading and no ligand included in the gel.

The effect of drug size on cumulative percentage release profiles for gels fabricated with a 5% loading of drug was studied individually and results are shown in FIG. 8. The release profiles for both BSA and IgG showed a relatively low initial burst (~22% for BSA and ~12% for IgG). This burst was followed by a period of decreasing release rate for a total release period of about 8 hours. This approximately exponential decrease in release rate is typical of that observed in the past for the diffusion-controlled, first-order release of macromolecules from hydrogels.

As can be seen in FIG. 8, protein release occurred rapidly, at least initially, followed by a period of continuously decreasing release rates. As the concentration of readily available drug present on the surface layers of the gels depleted, the rate of drug release became more dependant on the decreasing concentration gradient affecting the drug deep inside the polymer network, resulting in a corresponding decrease in release rate.

As can be seen in the Figure, incomplete release profiles were obtained in both the release experiments (i.e., not all of the encapsulated protein was released). One possible explanation for this behavior was the permanent immobilization of the drug molecules through a conjugate addition reaction between the double bonds present on any unreacted PEG DA macromers present inside the hydrogel and the thiol or amine groups present on the protein surface. These undesirable reactions can immobilize the drug within the hydrogel resulting in a permanent and incomplete protein release. Finally, any side reactions occurring during network formation involving the encapsulated proteins may lead to the denaturing of those proteins and a loss of signal during quantification.

Figure 9:
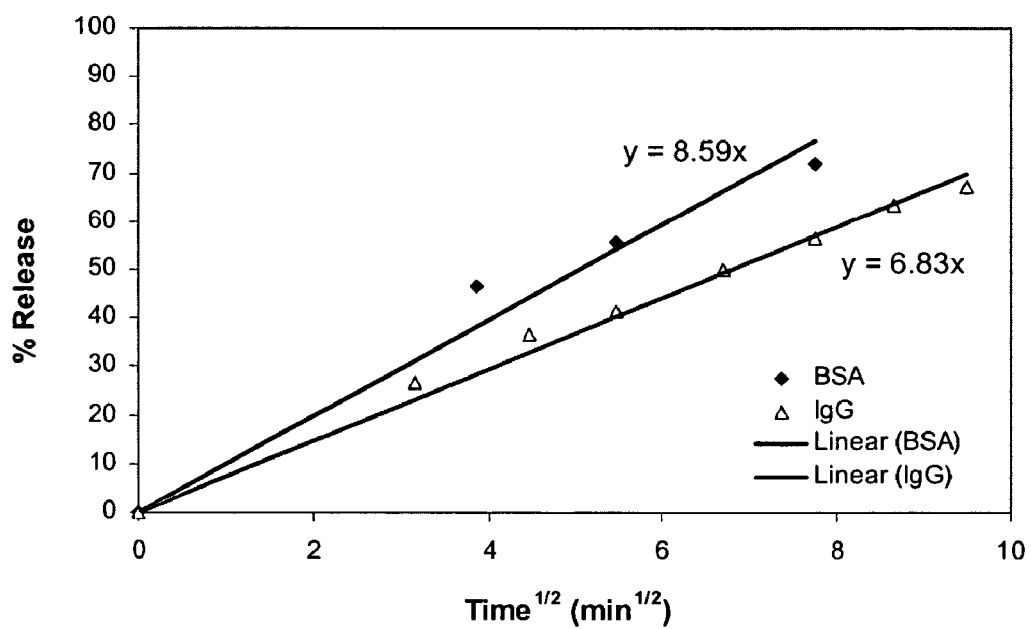
FIG. 9 graphically illustrates the release profiles of FIG. 8 plotted against time to the ½ power to demonstrate diffusion-controlled release of bovine serum albumin (BSA) and immunoglobulin G (IgG)

The percent drug release for both BSA and IgG were also plotted against time$^{1/2}$. Results are graphically illustrated in FIG. 9. As can be seen, in this system, the percent release rates remained constant with respect to the square root of time, clearly illustrating, and in accord with systems exhibiting Fickian Diffusion, that the dominant physical mechanism controlling drug release from these hydrogels was diffusion.

Example 2

Figure 10:
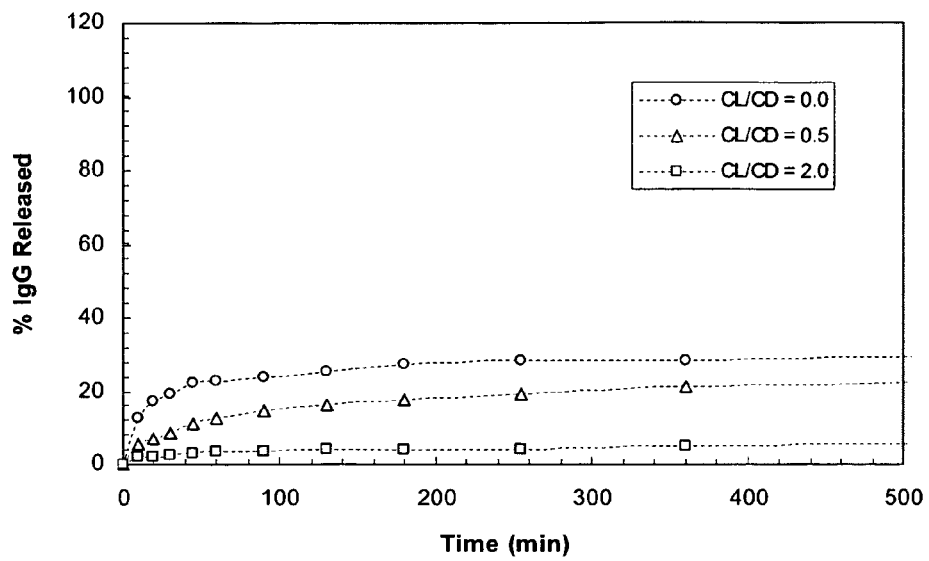
FIG. 10 graphically illustrates the cumulative percentage release of IgG from 10 wt % PEG 3400 DA gel with a 5 wt % drug loading at three different ligand/drug molar concentration ratios.

Release studies described in Example 1 were extended by copolymerizing 2-methacryloaminohistidine (MAH) into the 10% PEG 3400 DA gels of Example 1 to investigate ligand-drug binding effects on release rates of BSA and IgG. FIG. 10 shows the cumulative release percentage of IgG from a hydrogel (5 wt % drug loading) incorporated with MAH at ligand-drug molar ratios of (A) 0.0 (B) 0.5 and (C) 2.0. Incomplete release profiles observed in this study were again attributed to side reactions involving the protein during hydrogel formation. As can be seen, IgG was released fastest from the MAH-free hydrogel, with the release becoming slower as the ligand-drug molar ratio increased. The release in the first case was controlled only by diffusion while release profiles in the second and third cases was governed by both (i) ligand-drug reversible interaction and (ii) subsequent diffusion of free IgG. (For the current example, it was assumed that after interaction with MAH, IgG was released in its unmodified state.) The histidine amino acid at the end of the MAH ligand is known to participate in a reversible interaction with the $F_c$ segment of IgG with the known dissociation constant $K_D$=1.8 E-6 mM (as described in 'Interaction of human immunoglobulin G with l-histidine immobilized onto poly(ethylene vinyl alcohol) hollow-fiber membranes,' Haupt, K., et al., J. Chrom. B, 1995, 674, 13-21, which is incorporated herein by reference). Thus, copolymerization of MAH within the PEG hydrogel served to immobilize freely diffusible IgG dispersed inside the gel to create a non-diffusible complex in an amount governed by the interaction equilibrium. This immobilization reduced the concentration gradient of the freely diffusible drug and resulted in a corresponding decrease in the release rate of IgG. This effect became more prominent as the amount of MAH relative to IgG molecules increased, as shown in FIG. 10.

As can be seen with reference to FIG. 10, the initial release burst was lowered significantly by the incorporation of MAH into the hydrogel. This result was attributed to the reversible interactions exhibited by the MAH present in the layers closer to the surface that minimized the immediate release of IgG present on the surface and layers close to the surface.

Figure 11:
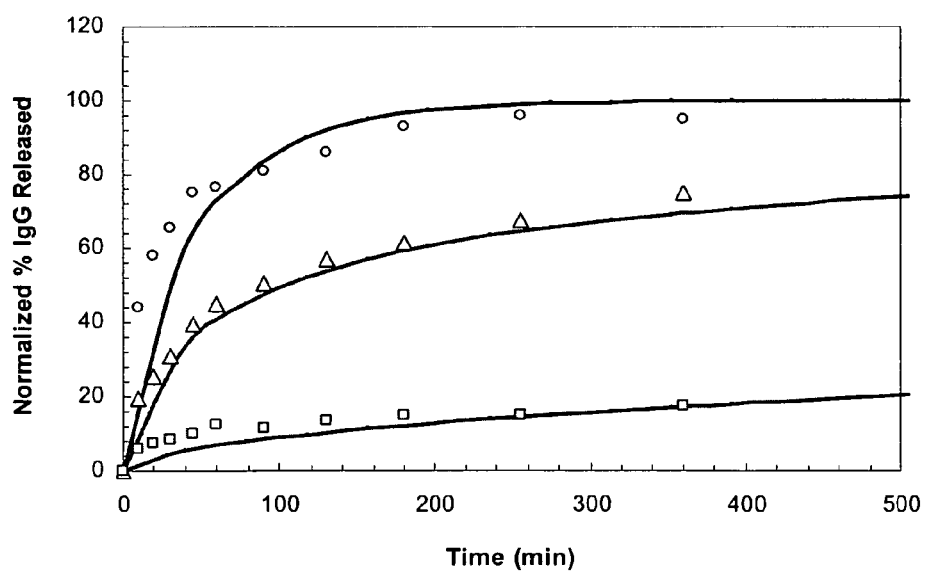
FIG. 11 illustrates the normalized experimental release percentages of FIG. 10 and compares the values obtained experimentally with theoretical predictions based on predetermined values of $C_L$ and $K_D$ (solid lines)

FIG. 11 shows the release profiles normalized against the cumulative release of IgG obtained by the end of the first 6 hours from the gel containing no ligand (Fractional release of ~28%). This plot represents the fractional release of IgG that was not immobilized permanently inside the hydrogel via undesirable side reactions and was released solely based on the effects of ligand-drug interaction and diffusion through the polymer matrix. As can be seen, IgG release rate was highly dependant upon the relative amount of MAH ligand present in the network. In addition, the experimentally determined data closely match the predicted values shown by the solid lines that were obtained according to the release model described in this invention.

Example 3

Figure 12:
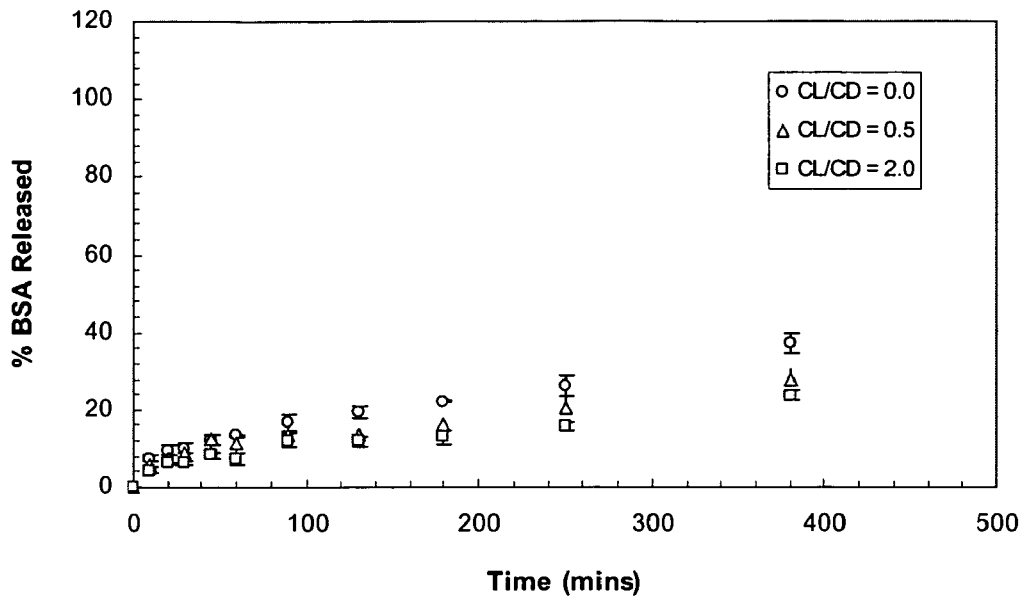
FIG. 12 graphically illustrates the cumulative percentage release of BSA from 10 wt % PEG 3400 DA gel with a 5 wt % drug loading at three different ligand/drug molar concentration ratios and represents a control study of the experiment described in FIG. 10.

Experiments were also performed to check the specificity of MAH towards IgG. Release experiments were performed in a manner similar to those described in Example 2 but with IgG replaced by BSA. FIG. 12 shows the release profiles for BSA from hydrogels functionalized with MAH at ligand-drug ratios of 0.0, 0.5 and 2.0.

Incomplete release of the drug was observed again, which was attributed to side reactions within the network. However, the presence of MAH did not affect the release rates of BSA significantly. The histidine tag on MAH exhibited affinity only to the Fc fragment of IgG and was hypothesized to remain inert or non-adhesive to BSA. Thus, the presence of MAH did not affect the release of BSA from the ligand-incorporated PEG gels. The release here was once again controlled only by diffusion, and the release rates were dependant on the relative sizes of drug and the network mesh.

Example 4

Di-acrylated poly (ethylene glycol) (PEGDA) was used as a macromer to form a hydrogel network via photopolymerization. PEGDA (10 wt %), BSA (10 wt %) and the photo-initiator Iracure 2959 (I-2959, 0.2 wt %) were mixed together in phosphate buffer solution (PBS, pH7.4). The mixed solution was exposed to UV radiation at a wavelength of 365 nm to rapidly form a protein-loaded hydrogel network of desired dimensions in a single step.

After photopolymerization, gels were placed in pH 7.4 PBS for in vitro protein release. Supernatant solution was sampled to quantify BSA cumulative release. The protein concentration was determined by fluorescamine staining.

Figure 13:
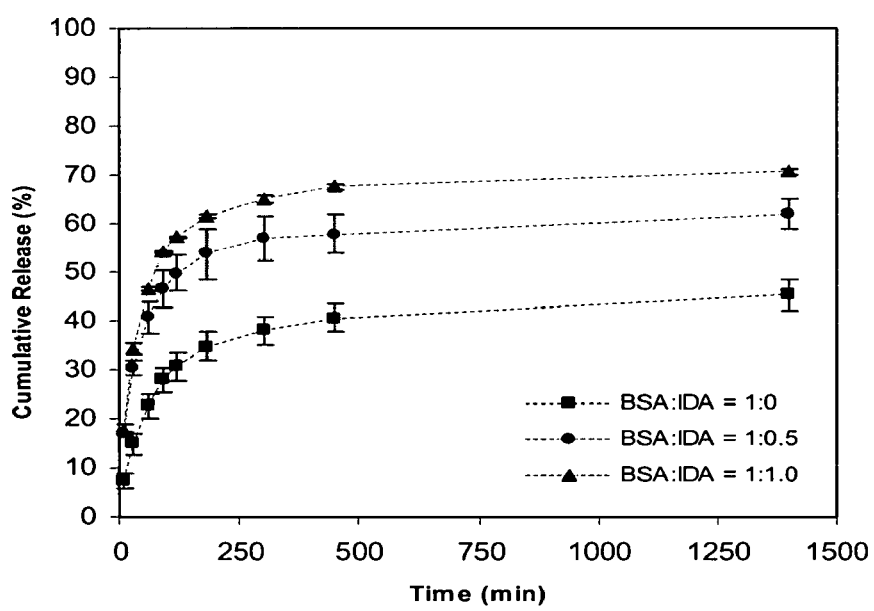
FIG. 13 graphically illustrates the cumulative percentage release of BSA from PEG hydrogel with various molar ratios of soluble iminodiacetic acid (IDA) ligand at 10 wt % protein loading.

Photopolymerization is a simple yet effective method for preparing protein-loaded hydrogels. However, during hydrogel fabrication, the protein is subjected to UV and free-radical exposure. Without proper protection, a substantial portion of the protein (e.g. 60% of the BSA as shown in FIG. 13) can be irreversibly immobilized within the hydrogel networks.

To increase the amount of the protein available for delivery and therefore improve therapeutic efficacy, iminodiacetic acid (IDA), which has an affinity for BSA, was incorporated as a protecting agent to prevent BSA from becoming denatured and/or permanently immobilized within the network. As shown in FIG. 13, when IDA was added into the mixed solution prior to photopolymerization, BSA released from the crosslinked hydrogel was enhanced to a final value of 70% as a function of IDA concentration.

Figure 14:
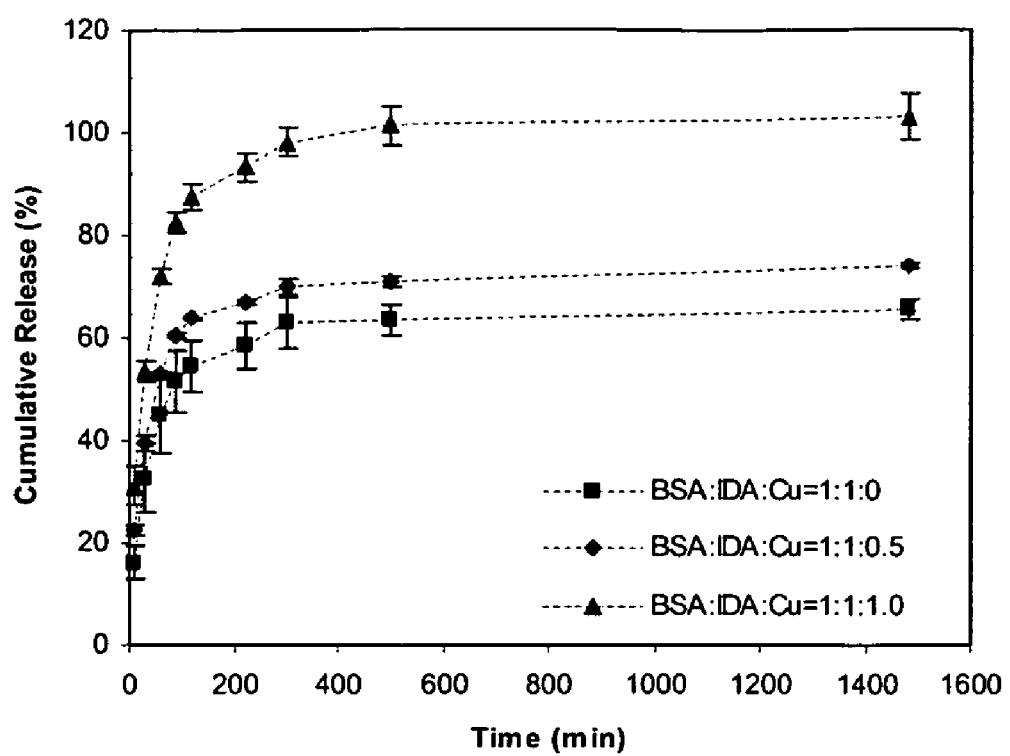
FIG. 14 graphically illustrates the systems of FIG. 13 with the inclusion of copper ions in the hydrogels.

Moreover, when $Cu^{2+}$, which facilitates tighter protein-ligand binding, was added into the pre-polymerization mixture, the cumulative release of BSA was further increased to effectively 100% (as can be seen in FIG. 14). The increased amount of BSA released was mainly due to the affinity between BSA and IDA. The addition of the divalent copper ion further increased the affinity. Note that in these cases, neither IDA nor the copper ions were immobilized into the network and therefore, as expected, did not affect BSA release rate from the matrix itself.

Thus, the formation of the ligand/drug complex as herein described can be used to protect the drug from side reactions prior to delivery of the drug to the target tissue. In addition, in those embodiments wherein the diffusion of the complex through the carrier matrix is prevented, such as through incorporation of the ligand within the matrix, the delivery rate of the drug from the matrix can be controlled due to the formation of the ligand/drug complex.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention that is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method for defining a controlled rate of release of a first biologically active agent from a polymeric carrier matrix comprising:
    forming a polymeric carrier matrix;
    loading an amount of a first polypeptide ligand into the polymeric carrier matrix, the first polypeptide ligand having an affinity for the first biologically active agent, the first biologically active agent being a protein; and binding at least a portion of the first biologically active agent to at least a portion of the first polypeptide ligand with a reversible, non-covalent bond between the first polypeptide ligand and the first biologically active agent to form a first polypeptide ligand/first biologically active agent complex, wherein the complex is formed prior to loading the first polypeptide ligand into the polymeric matrix, the affinity of the first polypeptide ligand for the first biologically active agent being described by an equilibrium dissociation constant, $K_D$ that is defined according to the equilibrium relationship:

$$\frac{[C_L][C_D]}{[C_{LD}]}$$

wherein
- $[C_L]$ is the concentration of the first polypeptide ligand in the polymeric carrier matrix that is not bound to first biologically active agent,
- $[C_D]$ is the concentration of the first biologically active agent in the carrier matrix that is not bound to first polypeptide ligand, and
- $[C_{LD}]$ is the concentration of the first polypeptide ligand/first biologically active agent complex in the polymeric carrier matrix; wherein the controlled rate of release of the first biologically active agent from the polymeric carrier matrix is defined by the value of the equilibrium dissociation constant.

2. The method according to claim 1, wherein the polymeric matrix is a degradable polymeric matrix.

3. The method according to claim 1, wherein the first polypeptide ligand is a fragment or a chimera of a naturally occurring protein.

4. The method according to claim 1, wherein the polymeric matrix defines a porosity that is larger than the size of the first biologically active agent.

5. The method according to claim 1, further comprising loading a second biologically active agent into the matrix.

6. The method according to claim 5, wherein the second biologically active agent is directly, reversibly, and non-covalently bound to the first ligand.

7. The method according to claim 5, further comprising loading a second ligand into the matrix, wherein the second biologically active agent is directly, reversibly, and non-covalently bound to the second ligand.

8. The method according to claim 1, further comprising encapsulating a living cell within the polymeric matrix.

9. The method according to claim 1, wherein the first biologically active agent is an unmodified protein therapeutic.

10. The method according to claim 1, wherein the polymeric matrix is a self-assembling matrix.

11. The method according to claim 1, further comprising locating the matrix adjacent a living cell.

12. The method according to claim 1, wherein the first polypeptide ligand is held within the polymeric matrix through hydrogen or ionic bonding.

13. The method according to claim 1, wherein the first polypeptide ligand is covalently bound within the polymeric matrix.

14. The method according to claim 1, wherein the complex is not bound to the polymeric matrix, the polymeric matrix defining a porosity that is less than the size of the complex, the complex being physically entrapped within the polymeric matrix.

15. The method according to claim 1, wherein the value of the equilibrium dissociation constant is less than about 1.0E+01 mM.

16. The method according to claim 15, wherein the value of the equilibrium dissociation constant is less than about 1.0E-05 mM.

17. The method according to claim 1, wherein the equilibrium dissociation constant is pH dependent.

18. A method for defining a controlled rate of release of a biologically active agent from a polymeric carrier matrix comprising:
- combining multifunctional monomers or macromers with a polymerization initiator;
- inducing the polymerization initiator to polymerize the multifunctional monomers or macromers to form a polymeric carrier matrix;
- loading an amount of a polypeptide ligand into the polymeric carrier matrix, the polypeptide ligand having an affinity for the biologically active agent; and
- binding at least a portion of the biologically active agent to at least a portion of the polypeptide ligand with a reversible, non-covalent bond between the polypeptide ligand and the biologically active agent to form a polypeptide ligand/biologically active agent complex, the biologically active agent being a protein, the affinity of the polypeptide ligand for the biologically active agent being described by an equilibrium dissociation constant, $K_D$ that is defined according to the equilibrium relationship:

$$\frac{[C_L][C_D]}{[C_{LD}]}$$

wherein
- $[C_L]$ is the concentration of the polypeptide ligand in the polymeric carrier matrix that is not bound to biologically active agent,
- $[C_D]$ is the concentration of the biologically active agent in the carrier matrix that is not bound to polypeptide ligand, and
- $[C_{LD}]$ is the concentration of the polypeptide ligand/biologically active agent complex in the polymeric carrier matrix; wherein the controlled rate of release of the biologically active agent from the polymeric carrier matrix is defined by the value of the equilibrium dissociation constant.

19. The method according to claim 18, wherein the polymerization initiator is a photoinitiator.

20. The method according to claim 18, wherein the polymerization initiator induces chemically activated polymerization.

21. The method according to claim 18, wherein the polymeric matrix is a degradable polymeric matrix.

22. The method according to claim 18, wherein the polymeric matrix defines a porosity that is larger than the size of the biologically active agent.

23. The method according to claim 18, further comprising encapsulating a living cell within the polymeric matrix.

24. The method according to claim 18, wherein the biologically active agent is an unmodified protein therapeutic.

25. The method according to claim 18, further comprising locating the matrix adjacent a living cell.

26. The method according to claim 18, wherein the polypeptide ligand is held within the polymeric matrix through hydrogen or ionic bonding.

27. The method according to claim 18, wherein the polypeptide ligand is covalently bound within the polymeric matrix.

28. The method according to claim 18, wherein the value of the equilibrium dissociation constant is less than about 1.0E+01 mM.

29. A method for defining a biphasic controlled rate of release of a biologically active agent from a polymeric carrier matrix comprising:

forming a polymeric carrier matrix;

loading an amount of a polypeptide ligand into the polymeric carrier matrix, the polypeptide ligand having an affinity for the biologically active agent, the biologically active agent being a protein;

loading an amount of the biologically active agent into the polymeric carrier matrix, wherein the ratio of the amount of the polypeptide ligand loaded into the polymeric carrier matrix to the amount of the biologically active agent loaded into the polymeric carrier matrix is less than unity;

binding at least a portion of the biologically active agent to at least a portion of the polypeptide ligand with a reversible, non-covalent bond between the polypeptide ligand and the biologically active agent to form a polypeptide ligand/biologically active agent complex, the affinity of the polypeptide ligand for the biologically active agent being described by an equilibrium dissociation constant, $K_D$ that is defined according to the equilibrium relationship:

$$\frac{[C_L][C_D]}{[C_{LD}]}$$

wherein

[$C_L$] is the concentration of the polypeptide ligand in the polymeric carrier matrix that is not bound to biologically active agent,

[$C_D$] is the concentration of the biologically active agent in the carrier matrix that is not bound to polypeptide ligand, and

[$C_{LD}$] is the concentration of the polypeptide ligand/biologically active agent complex in the polymeric carrier matrix; wherein the first phase of the biphasic controlled rate of release of the biologically active agent from the polymeric carrier matrix is defined by the rate of diffusion from the carrier matrix of the biologically active agent in the carrier matrix that is not bound to polypeptide ligand and the second phase of the biphasic controlled rate of release of the biologically active agent from the polymeric carrier matrix is defined by the value of the equilibrium dissociation constant.

30. The method according to claim 29, wherein the polymeric matrix is a degradable polymeric matrix.

31. The method according to claim 29, wherein the polypeptide ligand is a fragment or a chimera of a naturally occurring protein.

32. The method according to claim 29, wherein the polymeric matrix defines a porosity that is larger than the size of the biologically active agent.

33. The method according to claim 29, further comprising encapsulating a living cell within the polymeric matrix.

34. The method according to claim 29, wherein the first biologically active agent is an unmodified protein therapeutic.

35. The method according to claim 29, wherein the polymeric matrix is a self-assembling matrix.

36. The method according to claim 29, further comprising locating the matrix adjacent a living cell.

37. The method according to claim 29, wherein the polypeptide ligand is held within the polymeric matrix through hydrogen or ionic bonding.

38. The method according to claim 29, wherein the polypeptide ligand is covalently bound within the polymeric matrix.

39. The method according to claim 29, wherein the complex is not bound to the polymeric matrix, the polymeric matrix defining a porosity that is less than the size of the complex, the complex being physically entrapped within the polymeric matrix.

40. The method according to claim 29, wherein the value of the equilibrium dissociation constant is less than about 1.0E+01 mM.

41. The method according to claim 29, wherein the value of the equilibrium dissociation constant is less than about 1.0E-05 mM.

42. The method according to claim 29, wherein the equilibrium dissociation constant is pH dependent.

* * * * *